US010702711B2

(12) United States Patent
Kundapur et al.

(10) Patent No.: US 10,702,711 B2
(45) Date of Patent: Jul. 7, 2020

(54) MINI-BEAM COLLIMATORS FOR MEDICAL LINEAR ACCELERATORS

(71) Applicant: Saskatchewan Cancer Agency, Regina (CA)

(72) Inventors: Vijayananda Kundapur, Saskatoon (CA); Gavin Cranmer-Sargison, Saskatoon (CA)

(73) Assignee: Saskatchewan Cancer Agency, Regina (CA)

( * ) Notice: Subject to any disclaimer, the term of this patent is extended or adjusted under 35 U.S.C. 154(b) by 400 days.

(21) Appl. No.: 15/735,806

(22) PCT Filed: Jun. 13, 2016

(86) PCT No.: PCT/CA2016/050679
§ 371 (c)(1),
(2) Date: Dec. 12, 2017

(87) PCT Pub. No.: WO2016/201557
PCT Pub. Date: Dec. 22, 2016

(65) Prior Publication Data
US 2020/0038685 A1    Feb. 6, 2020

Related U.S. Application Data

(60) Provisional application No. 62/175,252, filed on Jun. 13, 2015.

(51) Int. Cl.
*A61N 5/10* (2006.01)
*G21K 1/02* (2006.01)

(52) U.S. Cl.
CPC ......... *A61N 5/1045* (2013.01); *A61N 5/1047* (2013.01); *G21K 1/025* (2013.01);
(Continued)

(58) Field of Classification Search
CPC ............... A61N 5/1045; A61N 5/1047; A61N 2005/1034; A61N 2005/1091; G21K 1/025
See application file for complete search history.

(56) References Cited

U.S. PATENT DOCUMENTS

2006/0176997 A1    8/2006    Dilmanian et al.

OTHER PUBLICATIONS

Uyama et al. "A narrow microbeam is more effective for tumor growth suppression than a wide microbeam", Journal of Synchrotron Radiation (2011), pp. 671-678.
(Continued)

*Primary Examiner* — Nicole M Ippolito
*Assistant Examiner* — Hanway Chang
(74) *Attorney, Agent, or Firm* — Todd A. Rattray, Oyen Wiggs Green & Mutala LLP

(57) ABSTRACT

An apparatus for delivery of spatially fractionated radiation treatment to a patient, the apparatus comprising: a radiation source for generating an open radiation beam oriented along a beam axis and having photon energies up to and including a maximum photon energy greater than 0.5 MV; a mini-beam collimator located in a path of the open radiation beam, the mini-beam collimator comprising a plurality of generally planar blades extending between an entrance aperture onto which the open beam impinges and an exit aperture, the mini-beam collimator interacting with the open radiation beam to produce an output beam emitted from the exit aperture, oriented along the beam axis and comprising a spatially fractionated mini-beam dose profile, the spatially fractionated mini-beam dose profile comprising: a plurality of dose peaks at which the dose is a local maximum, the dose peaks spaced apart from one another in a transverse direction that is transverse to the beam axis; and a plurality of dose valleys at which the dose is a local minimum, each dose
(Continued)

valley located between a pair of transversely adjacent dose peaks.

27 Claims, 15 Drawing Sheets

(52) U.S. Cl.
CPC ............... *A61N 2005/1034* (2013.01); *A61N 2005/1091* (2013.01)

(56) References Cited

OTHER PUBLICATIONS

Dilmanian, et al. "X-ray microbeams: Tumor therapy and central nervous system research", Nucl Instrum Methods Phys Res A. Aug. 11, 2005; 548(1-2): 30-37.
Cranmer-Sargison et al. "Medical linear accelerator mounted mini-beam collimator: design, fabrication and dosimetric characterization". Physics in Medicine and Biology, vol. 60, No. 17, Aug. 25, 2015, pp. 6991-7005.
Davis et al. "Medical linear accelerator mounted mini-beam collimator: transferability study". Monday, Jun. 15, 2015, URL: https://indico.cern.ch/event/355942/contributions/841248/attachments/707012/970631/2015_Presentation_v9.pdf Accessed online on Jul. 21, 2016.
Babcock et al. "Collimator design for experimental minibeam radiation therapy". Med. Phys. 38 (4), Apr. 2011, pp. 2192-2197.
Prezado et al. "X-ray energy optimization in minibeam radiation therapy". Med. Phys. 36(11), Nov. 2009, pp. 4897-4902.
Santos et al. "Proton and photon Minibeam Radiation Therapy (MBRT): a micro and nanodosimetry Monte Carlo Study". Radiotherapy and Oncology, vol. 115, Supplement 1, 3rd ESTRO Forum 2015, Apr. 2015, pp. S77, OC-0158 (starts at the bottom of the first column of p. S77).
Fois, "Monte Carlo simulation studies for spatially fractionated radiation therapy techniques". Thesis, Universita di Cagliari, 837, Apr. 3, 2013.
Dilmanian et al. "Interlaced x-ray microplanar beams: A radiosurgery approach with clinical potential". PNAS, vol. 103, No. 25, Jun. 20, 2006, pp. 9709-9714.
Buckey et al. "Evaluation of a commercially-available block for spatially fractionated radiation therapy". Journal of Applied Clinical Medical Physics, vol. 11, No. 3, Summer 2010, pp. 2-11.
Gokeri et al. "Monte Carlo simulation of stereotactic microbeam radiation therapy: evaluation of the usage of a linear accelerator as the x-ray source". Phys. Med. Biol. 58, (2013). pp. 4621-4642.
Crosbie et al. "Tumor cell response to synchrotron microbeam radiation therapy differs markedly from cells in normal tissues". International Journal of Radiation Oncology Biology Physics. (2010). pp. 886-894.
Dilmanian et al. "Response of rat intracranial 9L gliosarcoma to microbeam radiation therapy". Neuro-Oncology, vol. 4. (2002). pp. 26-30.
Laissue et al. Neuropathology of ablation of rat gliosarcomas and contiguous brain tissues using a microplanar beam of synchrotron-wiggler-generated X rays. International Journal of Cancer, 78(5). (1998). pp. 654-660.
Seco et al. Monte Carlo Techniques in Radiation Therapy. Boca Raton : CRC Press. (2013).
Alexander et al. "MMCTP: a radiotherapy research environment for Monte Carlo and patient-specific treatment planning". Phys Med Biol 52(13). (2007).
Wouters, Book excerpt titled "Cell death after irradiation: how, when and why cells die". pp. 27-40.
Brauer-Kriscia et al. "Characterization of a tungsten/gas multislit collimator for microbeam radiation therapy at the European Synchrotron Radiation Facility". Review of Scientific Instruments 76, 064303. (2005).
Alfonso et al. "A new formalism for reference dosimetry of small and nonstandard fields". Medical Physics, vol. 35, 5179. (2008).
Almond et al. "AAPM's TG-51 protocol for clinical reference dosimetry of high-energy photon and electron beams". Medical Physics, 26(9). (1999). pp. 1847-1870.
Anderson et al. "Evaluation of dose-vol. metrics for microbeam radiation therapy dose distributions in head phantoms of various sizes using Monte Carlo simulations". Physics in Medicine and Biology. (2012). pp. 3223-3248.
Andreo. "On the beam quality specification of high-energy photons for radiotherapy dosimetry". Medical Physics, 27(3). (2000). pp. 434-440.
Babcock et al. "An enhanced Howfarless option for DOSXYZnrc simulations of slab geometries". Medical Physics, 35(9). (2008). pp. 4106-4111.
Balagamwala et al. "Principles of Radiobiology of Stereotactic Radiosurgery and Clinical Applications in the Central Nervous System". Technology in Cancer Research and Treatment, 11(1). (2012).
Beddar et al. "Absorbed dose perturbation caused by diodes for small field photon dosimetry". Medical Physics, 21(7). (1994). pp. 1075-1079.
Brauer-Krisch et al. "Exploiting geometrical irradiation possibilities in MRT application". Nuclear Instruments and Methods in Physics Research Section A: Accelerators, Spectrometers, Detectors and Associated Equipment, 548(1-2). (2005). pp. 69-71.
Brauer-Krisch et al. "Effects of pulsed, spatially fractionated, microscopic synchrotron X-ray beams on normal and tumoral brain tissue". Mutation Research/Reviews in Mutation Research, 704(1-3). (2010). pp. 160-166.
Charles et al. "A practical and theoretical definition of very small field size for radiotherapy". Medical Physics, 41(4). (2014). p. 041707.
Cranmer-Sargison et al. "A methodological approach to reporting corrected small field relative outputs". Radiotherapy and Oncology, 109(3). (2013). pp. 350-355.
Cranmer-Sargison et al. Implementing a newly proposed Monte Carlo based small field dosimetry formalism for a comprehensive set of diode detectors. Medical Physics, vol. 38. (2011b). p. 6592.
Cranmer-Sargison et al. "Experimental small field 6 MV output ratio analysis for various diode detector and accelerator combinations". Radiother Oncol, 100. (2011a). pp. 429-435.
Cranmer-Sargison et al. "OC-0513 Diode detector modelling for small field dosimetry and correction factor sensitivity to source parameterization". Radiotherapy and Oncology, 103, Supplement 1. (2012). p. S206.
Das et al. "Small fields: Nonequilibrium radiation dosimetry". Med Phys, 35. (2008). pp. 206-215.
Francescon et al. "Calculation of k_(Q_clin,Q_msr)(f_clin,f_msr ) for several small detectors and for two linear accelerators using Monte Carlo simulations". Medical Physics, vol. 38. (2011). pp. 6513.
Klein et al. "Task Group 142 report: quality assurance of medical accelerators". Med Phys, Sep. 36(9). (2009). pp. 4197-4212.
Meigooni et al. "Dosimetric characteristics of a newly designed grid block for megavoltage photon radiation and its terapeutic advantage using a linear quadratic model". Med Phys, 33(9). (2006). pp. 3165-3173.
Mohiuddin et al. High-dose spatially-fractionated radiation (GRID): a new paradigm in the management of advanced cancers. Int J Radiat Oncol Biol Phys, 45(3). (1999). pp. 721-727.
Rogers et al. "BEAM: A Monte Carlo code to simulate radiotherapy treatment units". Medical Physics, 22(5). (1995). pp. 503-524.
Rogers et al. "BEAMnrc Users Manual". 2011. URL: http://www.irs.inms.nrc.ca/inms/irs/BEAM/beamhome.html. Accessed online at least as early as Sep. 1, 2012.
Scott et al. "Characterizing the influence of detector density on dosimeter response in non-equilibrium small photon fields". Phys Med Biol, 57(14). (2012). pp. 4461-4476.
Serduc et al. Synchrotron microbeam radiation therapy for rat brain tumor palliation—influence of the microbeam width at constant valley dose. Physics in Medicine and Biology. (2009).

(56) References Cited

OTHER PUBLICATIONS

Serduc et al. "High-precision radiosurgical dose delivery by interlaced microbeam arrays of high-flux low-energy synchrotron x-rays". PLoS One, 5(2). (2010).
Slatkin et al. "Microbeam radiation therapy". Medical Physics, 19(6). (1992). pp. 1395-1400.
Alexander et al. "Dosimetric effect of jaws for small MLC fields in 6 and 15 MV photon beam". Medical Physics 32(6). (2005).
Alexander et al. "Dosimetric effect of collimating jaws for small multileaf collimated fields". Medical Physics 32(3). (2005). pp. 759-765.
Slatkin et al. "Dual energy iodine contrast CT with monochromatic X-rays". Conference: Nuclear Science Symposium and Medical Imaging Conference Record, 1995. 1995 IEEE, vol. 3.
Slatkin et al. "Subacute Neuropathological Effect of Microplanar Beams of X-Rays from a Synchrotron Wiggler". Proceedings of the National Academy of Sciences 92(19). (1995) pp. 8783-8787.
Slatkin et al. "Multiple energy computed tomography (MECT) at the NSLS: Status report". Review of Scientific Instruments 66(2). (1995). pp. 1346-1347.
Slatkin et al. "Design of a multislit, variable width collimator for microplanar beam radiotherapy". Review of Scientific Instruments 66(2). (1995). pp. 1459-1460.
Cranmer-Sargison et al. Poster titled "Spatially Fractionated Radiotherapy Using a Medical Linear Accelerator Mounted Mini-Beam Collimator".
Alexander et al. Poster titled "Treatment planning study for spatially fractionated mini-beam radiotherapy".

MINI-BEAM COLLIMATORS FOR MEDICAL LINEAR ACCELERATORS

REFERENCE TO RELATED APPLICATIONS

This application claims priority from U.S. application No. 62/175,252 filed 13 Jun. 2015, which is hereby incorporated herein by reference.

TECHNICAL FIELD

This invention relates to the delivery of radiation for medical purposes, and particularly to apparatus and methods for delivering radiation to cancerous tumors.

BACKGROUND

Radiation therapy is a known treatment for cancerous tumors. Radiation therapy aims to deliver high doses of radiation to tumor volumes. A challenge in treating cancerous brain tumors lies in effectively eradicating the tumor volume while minimizing damage to healthy cells which may be located adjacent or proximate to the cancerous tumor. Conventional radiation treatment is associated with collateral damage to healthy cells. In long term survivors, this may manifest as varying combinations of neurocognitive/neuropsychological problems, endocrine/visual/auditory deficits, impaired bone growth, second malignancies and/or other problems.

Synchrotron-generated micro-beam radiation therapy has been used to treat cancerous brain tumors in small animals. Synchrotron-generated micro-beam radiation therapy uses radiation from a synchrotron source which is collimated to provide a spatially fractionated radiation profile comprising an array of micro-beams. Because of their synchrotron-based radiation source, synchrotron-generated micro-beam radiation therapy uses relatively low energy radiation beams. Synchrotron-generated radiation beams are typically ≤200 keV and are collimated into an array of micro-beams having micro-beam widths in the range of approximately 25-75 μm separated by peak-to-peak separation distances in the range of approximately 100-400 μm.

Synchrotron-generated micro-beam radiation therapy techniques have shown promising results in preserving brain architecture while killing tumor cells in small animal models. In particular, synchrotron-generated micro-beam radiation therapy techniques have shown a higher therapeutic index (ratio of maximum dose tolerated by normal tissue to minimum dose required to control the tumor) than that of conventional radiation therapy methods. Despite the promising results shown in small animal models, the physical characteristics of synchrotron-generated micro-beam radiation therapy techniques limit its use for human patients. Synchrotron-generated micro-beam radiation therapy techniques utilize a low energy photon source (the synchrotron) and micro-beams being made up of such low energy photons have limited ability to penetrate to a sufficient depth within the tissue of humans or other large mammals. The limited depth of penetration associated with the low energy photons of synchrotron-generated micro-beam radiation therapy is not sufficient to destroy tumors embedded deeper in the bodies of humans or other larger mammals. Further, synchrotron radiation sources are often located only in large facilities and such facilities are geographically spaced apart (and thus are not conveniently available). Still further, synchrotron radiation sources are expensive and have rudimentary control systems, which limit the use of these synchrotron sources for medical procedures.

Grid therapy techniques have been suggested for medical linear accelerator (LINAC) based photon radiation in the megavolt energy range. The grid therapy compensator block (or multi-leaf collimator arrangement) has typically been designed to produce a minimum hexagonal array of high dose peaks 1.0 cm in diameter projected at isocenter with a center-to-center grid spacing of 2.0 cm. While LINAC-based grid therapy techniques use X-ray energies high enough to provide sufficient depth of penetration in humans, such large center-to-center grid spacing produced by grid therapy techniques would typically be limited to treating large and bulky tumor volumes, and would not provide a therapeutic index high enough for the treatment of typical brain tumors.

There remains a desire for an apparatus and method for delivery of spatially fractionated radiation treatment that has sufficient depth of tissue penetration for therapeutic use on large mammals, such as humans. More particularly, there is a desire for such radiation treatment to yield a high therapeutic index as may be desired for tumors located in a human brain.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides an apparatus for delivery of spatially fractionated radiation treatment to a patient. The apparatus includes a radiation source for generating an open radiation beam and a mini-beam collimator. The open radiation beam is oriented along a beam axis and has photon energies up to and including a maximum photon energy. The maximum photon energy is greater than 0.5 MV. The mini-beam collimator is located in a path of the open radiation beam. The mini-beam collimator includes a plurality of generally planar blades which extend between an entrance aperture onto which the open beam impinges and an exit aperture. The mini-beam collimator interacts with the open radiation beam to produce an output beam which is emitted from the exit aperture. The output beam is oriented along the beam axis and includes a spatially fractionated mini-beam dose profile. The spatially fractionated mini-beam dose profile comprises a plurality of dose peaks at which the dose is a local maximum and a plurality of dose valleys at which the dose is a local minimum. The dose peaks are spaced apart from one another in a transverse direction that is transverse to the beam axis, and each dose valley is located between a pair of transversely adjacent dose peaks.

In some embodiments, the apparatus includes a beam-movement mechanism for moving the beam axis about an isocenter so that the beam axis interacts with the isocenter during the movement. The isocenter may be spaced apart along the beam axis from the exit aperture of the collimator.

In some embodiments, the radiation source of the apparatus is a medical linear accelerator, and the beam-movement mechanism is a moveable treatment head of the medical linear accelerator.

In some embodiments, the maximum photon energy of the output radiation beam generated by the radiation source of the apparatus is in a range of 4 MV-25 MV. In some embodiment, the maximum photon energy of the output radiation beam generated by the radiation source of the apparatus is in a range of 4 MV-10 MV. In some embodiment, the maximum photon energy of the output radiation beam generated by the radiation source of the apparatus is in a range of 10 MV-25 MV.

In some embodiments, the radiation source of the apparatus is a Cobalt-60 radiation source. The maximum photon energy of the output radiation beam energy generated by the Cobalt-60 radiation source may be in a range of 4 MV-10 MV.

In some embodiments, the mini-beam collimator comprises a central collimator axis about which the blades are symmetrically located. The collimator may be located so that the central collimator axis is aligned with the beam axis. The central collimator axis may extend through a central air gap of the collimator between the entrance aperture and the exit aperture.

In some embodiments, the blades may be spaced apart from one another in the transverse direction by air gaps. The blades may be oriented such that widths of the air gaps in the transverse direction at the exit aperture are greater than widths of the air gaps in the transverse direction at the entrance aperture.

In some embodiments, the blades are oriented at a variety of angles relative to the collimator axis. A transversely outermost pair of blades may be respectively oriented at angles $+/-\theta$ relative to the collimator axis, where $\theta$ corresponds to the divergence angle of the open beam. The blades may be oriented at evenly angularly spaced apart intervals between $-\theta$ and $+\theta$ relative to the collimator axis.

In some embodiments, a width of the air gaps in the transverse direction is equal to a width of the blades in the transverse direction at the exit aperture.

In some embodiments, the blades comprise lengths in directions of extension of the blades between the entrance aperture and the exit aperture in a range of 1 cm-25 cm. In some embodiments, the blades comprise lengths in directions of extension of the blades between the entrance aperture and the exit aperture in a range of 2 cm-10 cm. In some embodiments, the blades comprise widths in directions transverse to their extension between the entrance aperture and the exit aperture in a range of 0.4 mm-6.0 mm.

In some embodiments, the blades comprise widths in directions transverse to their extension between the entrance aperture and the exit aperture in a range of 0.6 mm-1.0 mm.

In some embodiments, the maximum photon energy of the open radiation beam is selected and the blades are shaped and located relative to the radiation source and the isocenter such that the valley-to-peak dose ratio, VPDR, of the mini-beam dose profile is less than 0.80 at a surface of the skin of the patient having a tumor located at the isocenter.

In some embodiments, the maximum photon energy of the open radiation beam is selected and the blades are shaped and located relative to the radiation source and the isocenter such that the valley-to-peak dose ratio, VPDR, of the mini-beam dose profile is less than 0.70 at a surface of the skin of the patient having a tumor located at the isocenter.

In some embodiments, the maximum photon energy of the open radiation beam is selected and the blades are shaped and located relative to the radiation source and the isocenter such that the valley-to-peak dose ratio, VPDR, of the mini-beam dose profile is less than 0.85 at a depth into the patient that is equivalent to a depth of 10 cm into water. Equivalent depths in water are used as a measure of effective penetration depth into the bodies of patients which accounts for the radiation transmission through non-water equivalent (but highly variable) materials that the beam may transverse, such as fat, bone, tissue, muscle and organ (e.g. lung).

In some embodiments, the maximum photon energy of the open radiation beam is selected and the blades are shaped and located relative to the radiation source and the isocenter such that the valley-to-peak dose ratio, VPDR, of the mini-beam dose profile is less than 0.80 at a depth into the patient that is equivalent to a depth of 10 cm into water.

In some embodiments, the maximum photon energy of the open radiation beam is selected and the blades are shaped and located relative to the radiation source and the isocenter such that a beam width of a central peak of the mini-beam dose profile in the transverse direction is in a range of 0.5 mm-2 mm at the isocenter.

In some embodiments, the maximum photon energy of the open radiation beam is selected and the blades are shaped and located relative to the radiation source and the isocenter such that a beam width of a central peak of the mini-beam dose profile in the transverse direction is in a range of 0.7 mm-1.5 mm at the isocenter.

In some embodiments, the maximum photon energy of the open radiation beam is selected and the blades are shaped and located relative to the radiation source and the isocenter such that a peak-to-peak separation between a central peak of the mini-beam dose profile and a transversely adjacent peak in the transverse direction is in a range of 1.5 to 5 times a beam width of the central peak in the transverse direction at isocenter.

In some embodiments, the maximum photon energy of the open radiation beam is selected and the blades are shaped and located relative to the radiation source and the isocenter such that a peak-to-peak separation between a central peak of the mini-beam dose profile and a transversely adjacent peak in the transverse direction is in a range of 2 to 4 times a beam width of the central peak in the transverse direction at isocenter.

In some embodiments, the entrance aperture of the collimator is located at a distance, along the beam axis, in a range of 40 cm-80 cm from the radiation source.

In some embodiments, the apparatus includes one or more adjustment mechanisms for locating the collimator relative to the radiation source. The one or more adjustment mechanisms may comprise one or more lateral adjustment mechanisms for adjusting a location of the central collimator axis relative to the beam axis in one or more transverse directions and one or more angular adjustment mechanisms for adjusting an orientation of the central collimator axis relative to the beam axis.

Another aspect of the invention provides a method for generating spatially fractionated radiation. The method includes generating an open radiation beam oriented along a beam axis, the open radiation beam comprising photon energies up to and including a maximum photon energy greater than 0.5 MV, positioning a mini-beam collimator in a path of the open radiation beam, the mini-beam collimator includes a plurality of generally planar blades extending between an entrance aperture onto which the open beam impinges and an exit aperture, and producing, by interaction of the mini-beam collimator with the open radiation beam, an output beam emitted from the exit aperture, oriented along the beam axis and comprising a spatially fractionated mini-beam dose profile. The spatially fractionated mini-beam dose profile comprises a plurality of dose peaks at which the dose is a local maximum, the dose peaks spaced apart from one another in a transverse direction that is transverse to the beam axis and a plurality of dose valleys at which the dose is a local minimum. Each dose valley is located between a pair of transversely adjacent dose peaks.

Another aspect of the invention provides a method for treating a tumor in a patient using spatially fractionated radiation. The method comprises generating an open radiation beam oriented along a beam axis and having photon energies up to and including a maximum photon energy greater than 0.5 MV, positioning a mini-beam collimator in a path of the open radiation beam, the mini-beam collimator comprising a plurality of generally planar blades extending between an entrance aperture onto which the open beam impinges and an exit aperture, producing, by interaction of the mini-beam collimator with the open radiation beam, an output beam emitted from the exit aperture, oriented along the beam axis and comprising a spatially fractionated mini-beam dose profile, and locating the patient along the beam axis, so that the output beam impinges on the patient, thereby delivering the spatially fractionated mini-beam dose profile to the patient. The spatially fractionated mini-beam dose profile includes a plurality of dose peaks at which the dose is a local maximum, the dose peaks spaced apart from one another in a transverse direction that is transverse to the beam axis and a plurality of dose valleys at which the dose is a local minimum, each dose valley located between a pair of transversely adjacent dose peaks.

In some embodiments, the method further comprises moving the beam axis about an isocenter so that the beam axis intersects with the isocenter during the movement, and locating the patient so that the isocenter is located in a volume of the tumor. The isocenter may be spaced apart along the beam axis from the exit aperture of the collimator Methods according to particular aspects of this invention includes any of the features described in the apparatus according to particular aspects of this invention.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIGS. 8A and 8B are collectively referred to as FIG. 8.

FIGS. 9A, 9B and 9C are collectively referred to as FIG. 9.

FIGS. 10A, 10B and 10C are collectively referred to as FIG. 10.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

This disclosure and the accompanying claims relate to the delivery of spatially fractionated radiation treatment which involves using a medical linear accelerator-based radiation source (or other radiation source which emits high energy photons) and a mini-beam collimator placed in a path of the beam emitted by the linear accelerator radiation source to generate an array of mini-beams.

Figure 1:
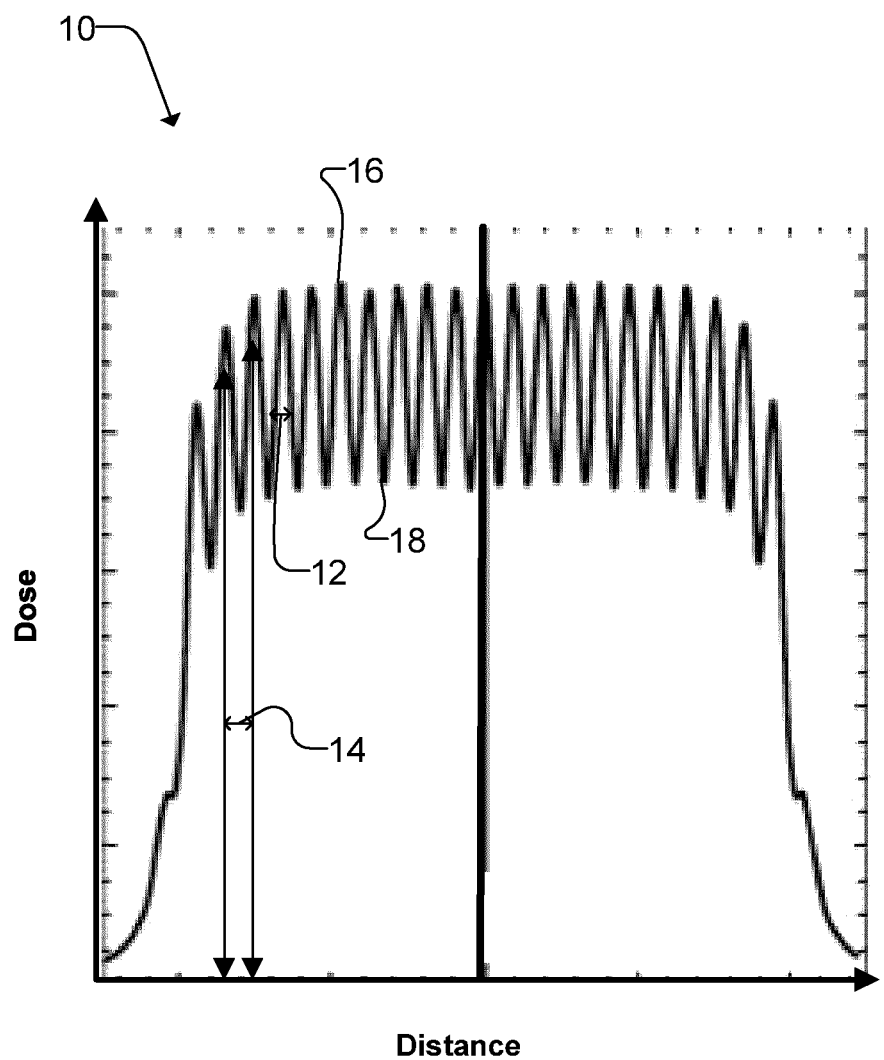
FIG. 1 is a plot illustrating an example of a spatially fractionated mini-beam dose profile according to an example embodiment of this invention.

Aspects of this disclosure provide methods and apparatus for generating mini-beam radiation for use in mini-beam radiation therapy. Mini-beam radiation comprises a radiation beam that is spatially fractionated into an array comprising a plurality of radiation "mini-beams". The array of mini-beams has a dose profile comprising high dose 'peaks' and low dose 'valleys'. An example of a mini-beam dose profile 10 is illustrated in FIG. 1. As shown in the FIG. 1 plot, the mini-beam dose profile comprises a series of dose peaks 16 and valleys 18 and the geometry of the mini-beam dose profile may be characterized by parameters which include: beam width 12, peak-to-peak separation distance 14, dose peaks 16 and dose valleys 18. For a particular individual mini-beam, its beam width 12 may be defined to the full spatial width of the peak at half maximum relative to the pair of adjacent valleys on either side of the peak. If the dose levels of the pair of adjacent valleys are different, then the average of the dose levels of the two adjacent valleys may be used to determine the half maximum of the peak. Typically, mini-beams have beam widths and peak-to-peak distances in the millimeter range. In some embodiments, the individual mini-beams in the array of mini-beams have beam widths in a range of 0.5 mm-2.0 mm at isocenter. In some embodiments, these beam widths are in a range of 0.7 mm-1.5 mm at isocenter. In some embodiments, these beam widths are in a range of 0.8 mm-1.2 mm at isocenter. In some embodiments, the peak-to-peak separation distances between individual mini-beams in the mini-beam array are in a range of 1.5 to 5 times the beam width of the individual mini-beams at isocenter. In some embodiments, this peak-to-peak separation is in a range of 2 to 4 times the beam width of the individual mini-beams at isocenter.

The spatially fractionated (peaks and valleys) dose distribution pattern in mini-beam radiation is a characteristic associated with improved therapeutic index, relative to radiation therapy using non-spatially fractionated radiation beams. Without wishing to be bound by theory, it is hypothesized that there are at least two reasons for the improved therapeutic effect of mini-beam radiation therapy. First, since healthy tissues have the ability to repair themselves and the low 'valley' dose does little damage to such tissues, it is thought that the healthy tissues that receive low 'valley' dose can help to repair neighboring tissues that receive high 'peak' dose. The second reason is that even tumor cells that receive low 'valley' dose may also be killed due to the "bystander effect". The "bystander effect" involves indirect killing of non-irradiated tumor cells (or tumor cells which receive low 'valley' dose), which is somehow induced or caused by neighboring irradiated tumor cells (or tumor cells which receive high 'peak' dose). It is hypothesized that the bystander effect may be caused, for example, by non-irradiated tumor cells receiving signals released by nearby irradiated tumor cells.

Another characteristic of the mini-beam radiation profile is the ratio between the dose at the central peak and the dose at neighboring valleys (or at the average of the neighboring valleys), which is referred to as the peak-to-valley dose ratio (PVDR). Although technically not a characteristic that is independent from the PVDR, the mini-beam radiation profile may also be characterized by the inverse of the PVDR (i.e. the valley-to-peak dose ratio (VPDR)). It has been hypothesized that the higher the PVDR, the lower the normal-tissue toxicity. Thus, a measure of PVDR has been proposed as an indication as to the therapeutic effect of a particular mini-beam dose profile—i.e. higher PVDR is associated with higher (and more desirable) therapeutic effect.

Figure 2:
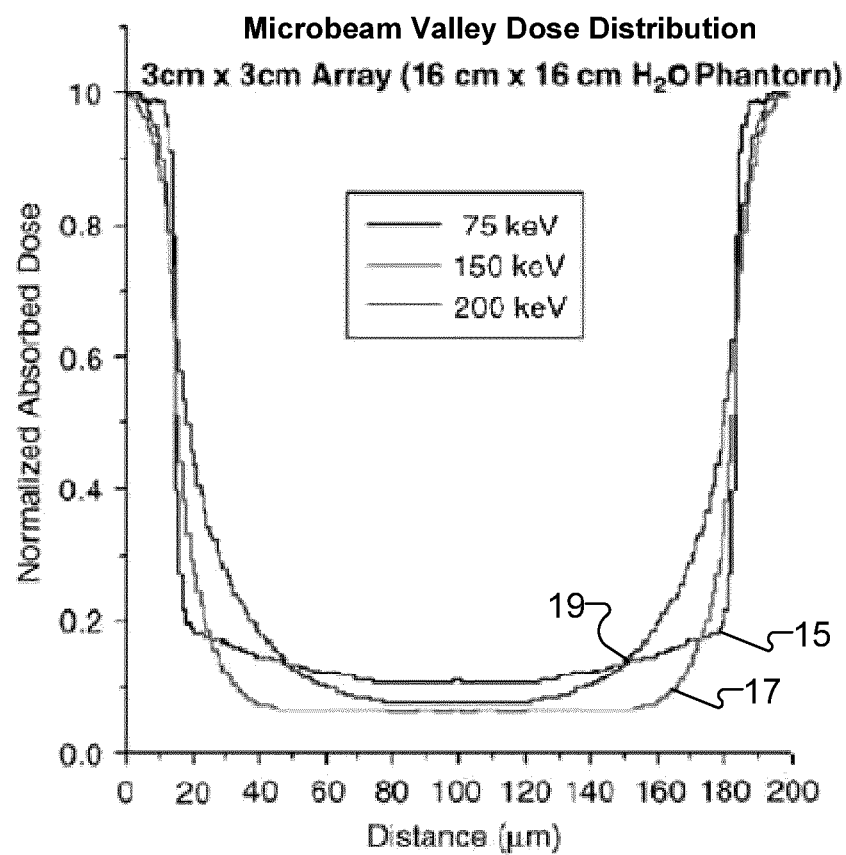
FIG. 2 illustrates the valley dose distributions of individual micro-beams generated from sources of different energy levels as reported by Dilmanian F. A., et al. "X-ray microbeams: Tumor therapy and central nervous system research" Nucl Instrum Methods Phys Res A. 548(1-2) (2005): 30-37.

While spatially fractionated micro-beam radiation profiles also exhibit peak and valley dose patterns (i.e., with individual beam widths in the range of approximately 25-75 µm wide that are separated by peak-to-peak separation distances in the range of approximately 100-400 µm), it is not possible to produce arrays of micro-beams from radiation sources having energies over 0.5 MeV (or from beams with photon energies over 0.5 MV), such as a medical linear accelerator source and its radiation beam, for example. Medical linear accelerators are typically designed to accelerate electrons to energies in the range of approximately 4 MeV-25 MeV. The accelerated electrons are then directed at a high-density target which results in a photon radiation beam with photons having energies up to and including the accelerated electron energy (e.g. photons having maximum energies on the order of 4 MV-25 MV). The invention need not be expressly limited to medical linear accelerator radiation sources, however. In some embodiments, the invention makes use of energy sources having energies in a range of up to and including energies of 0.5 MeV-25 MeV. In some embodiments, the energies of the radiation sources are in a range of up to and including 0.5 MeV-4 MeV. In some embodiments, the energies of the radiation sources are in a range of up to and including 4 MeV-10 MeV. In some embodiments, the energies of the radiation sources are in a range of up to and including 10 MeV-25 MeV. It is believed that micro-beam radiation profiles cannot be generated using the high energy radiation beams typically emitted by linear accelerators (e.g. beams with typical maximum photon energies of over 4 MV) or even with other high energy radiation beams with maximum photon energies of over 0.5 MV, because the high energy photons "wash out" the peak and valley dose patterns of the micro-beam dose profile. In particular, studies have shown that at higher beam energies, the micro-beam configuration reveals considerable rounding of the edges of the valley dose region (as shown in FIG. 2). The desired configuration of valley dose regions comprises a generally rectangular-shape, as illustrated in the exemplary micro-beam dose distribution generated by the low 75 keV beam energy (plot 15) in FIG. 2. Increased rounding of these "corners" is exhibited by the dose distribution for 150 keV (plot 17) and further increased rounding is exhibited by the dose distribution for 200 keV (plot 19). It will be appreciated that extensive rounding of the edges of the valley regions would eventually lead to the elimination of the desired valley dose regions. Without the desired valley dose regions, such radiation therapy would not be spatially fractionated and would not exhibit the above-discussed features (the healthy tissue repairing effect and the bystander effect) which make spatially-fractionated radiation therapy desirable for treating cancerous tumors. This "washing out" of the peak and valley dose profile at high energies sets an upper beam energy limit for micro-beam radiation (having beam widths less than 75 µm and peak-to-peak separation distance less than 400 µm). Typically, it is known in the art that the upper beam energy limit for micro-beam radiation therapy is around 250 keV.

The inventors have discovered that a spatially fractionated array of mini-beams having a dose profile comprising peak and valley patterns can be generated by higher energy radiation sources (e.g. radiation sources, such as medical linear accelerators or other high energy radiation sources such as a Cobalt 60 teletherapy unit, which generate beams having average photon energies over 0.5 MV) using a collimator designed to generate an array of mini-beams, where individual mini-beams in the resultant mini-beam dose profile are wider and further spaced apart from one another than individual micro-beams in a micro-beam dose profile). In some embodiments, the individual mini-beams in the array of mini-beams have beam widths in a range of 0.5 mm-2.0 mm at isocenter. In some embodiments, these beam widths are in a range of 0.7 mm-1.5 mm at isocenter. In some embodiments, these beam widths are in a range of 0.8 mm-1.2 mm at isocenter. In some embodiments, the peak-to-peak separation distances between individual mini-beams in the mini-beam array are in a range of about 1.5-5 times the beam width of the individual mini-beams at isocenter. In some embodiments, this peak-to-peak separation distances is in a range of 2 to 4 times the beam width of the individual mini-beams at isocenter.

Figure 3:
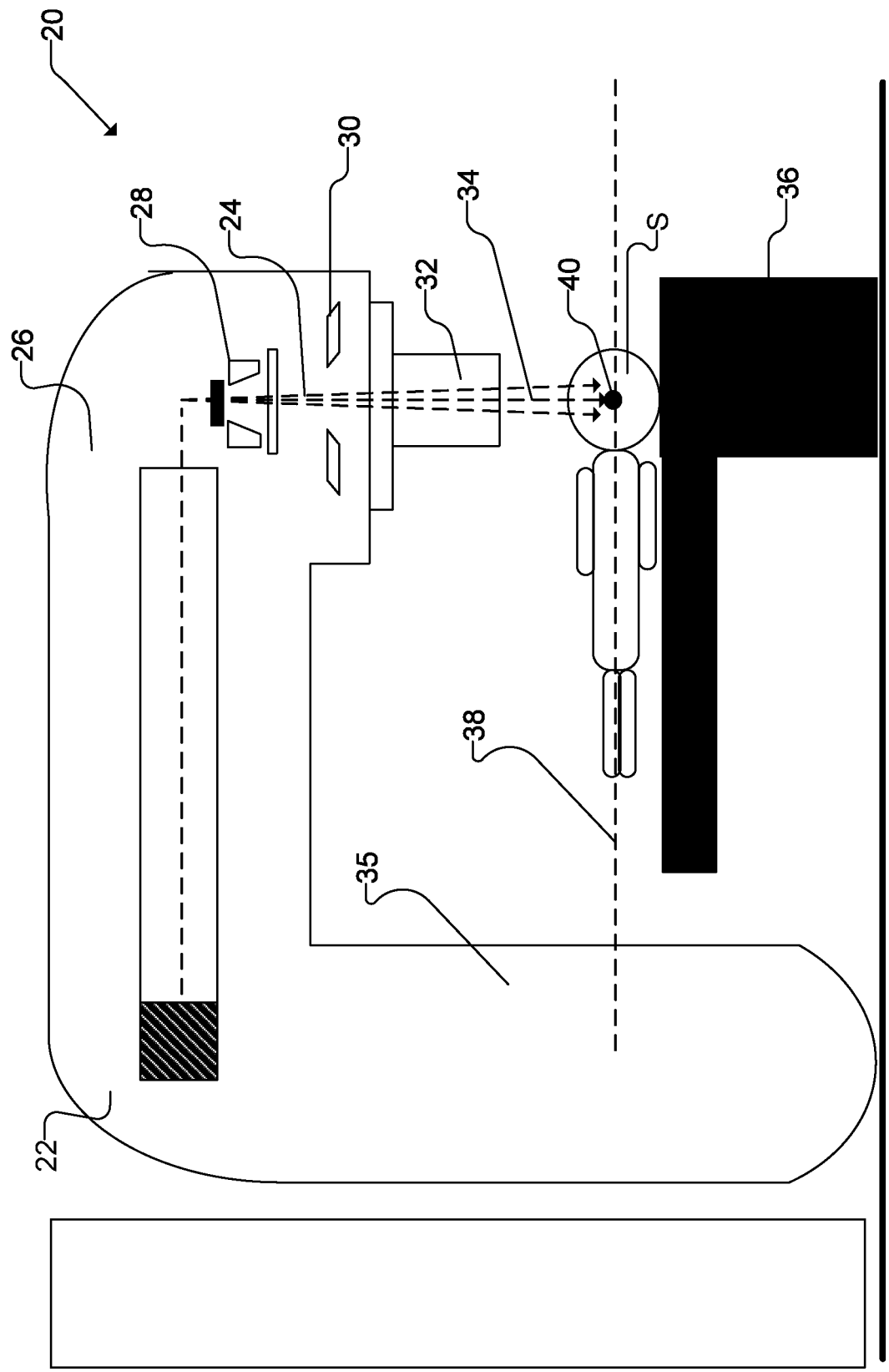
FIG. 3 is a schematic view of a medical linear accelerator in conjunction with a mini-beam collimator according to an exemplary embodiment.

FIG. 3 illustrates a system 20 for the delivery of spatially fractionated mini-beam radiation treatment to a patient. System 20 comprises a linear accelerator 22 as a radiation source. Linear accelerator 22 is controllably operable to emit an open radiation beam 24 from an opening of a treatment head 26. In some embodiments, open radiation beam 24 may have maximum photon energies in a range of 4 MV-25 MV, although this is not necessary and, in some embodiments, the photon energies used may be in other ranges described herein. Treatment head 26 comprises components in the path of open radiation beam 24 which are designed to shape open radiation beam 24. In particular, treatment head 26 may comprise a plurality of collimators. In some embodiments, treatment head 26 comprises a primary collimator 28 and a secondary collimator 30 (collectively referred to as internal collimators 28, 30). One or both internal collimators 28, 30 may be manually or automatically adjusted to vary the cross-sectional area of the output beam "window" through which radiation is emitted from treatment head 26.

System 20 also includes a mini-beam collimator that is located in the path of open radiation beam 24. In some embodiments, mini-beam collimator 32 is mounted on treatment head 26, but mini-beam collimator 32 may be otherwise located in the path of open radiation beam 24 to provide the functionality described herein. Mini-beam collimator 32 may be positioned below internal collimators 28, 30 so that open radiation beam 24 enters mini-beam collimator 32 after travelling through internal collimators 28, 30. As discussed in more detail below, mini-beam collimator 32 is shaped to generate an output beam 34 having a spatially fractionated mini-beam dose profile exhibiting a peak and valley dose distribution pattern.

As shown in FIG. 3, subject S may be positioned on a table or a couch 36 or may be otherwise located in the path of output beam 34. System 20 comprises a number of moveable components that permit the orientation of the output beam 34 to be moved relative to subject S. An example of such component in the FIG. 3 embodiment is a gantry 35. Gantry 35 can be rotated about an axis 38. Axis 38 and the output beam 34 intersect at an isocenter 40. Other moveable components, such as couch 36, can also be manipulated to change the location of subject S relating to output beam 34. Output beam 34 can thus be projected at the desired location of the tumor volume of the subject S by manipulating the moveable components of system 20.

Figure 4:
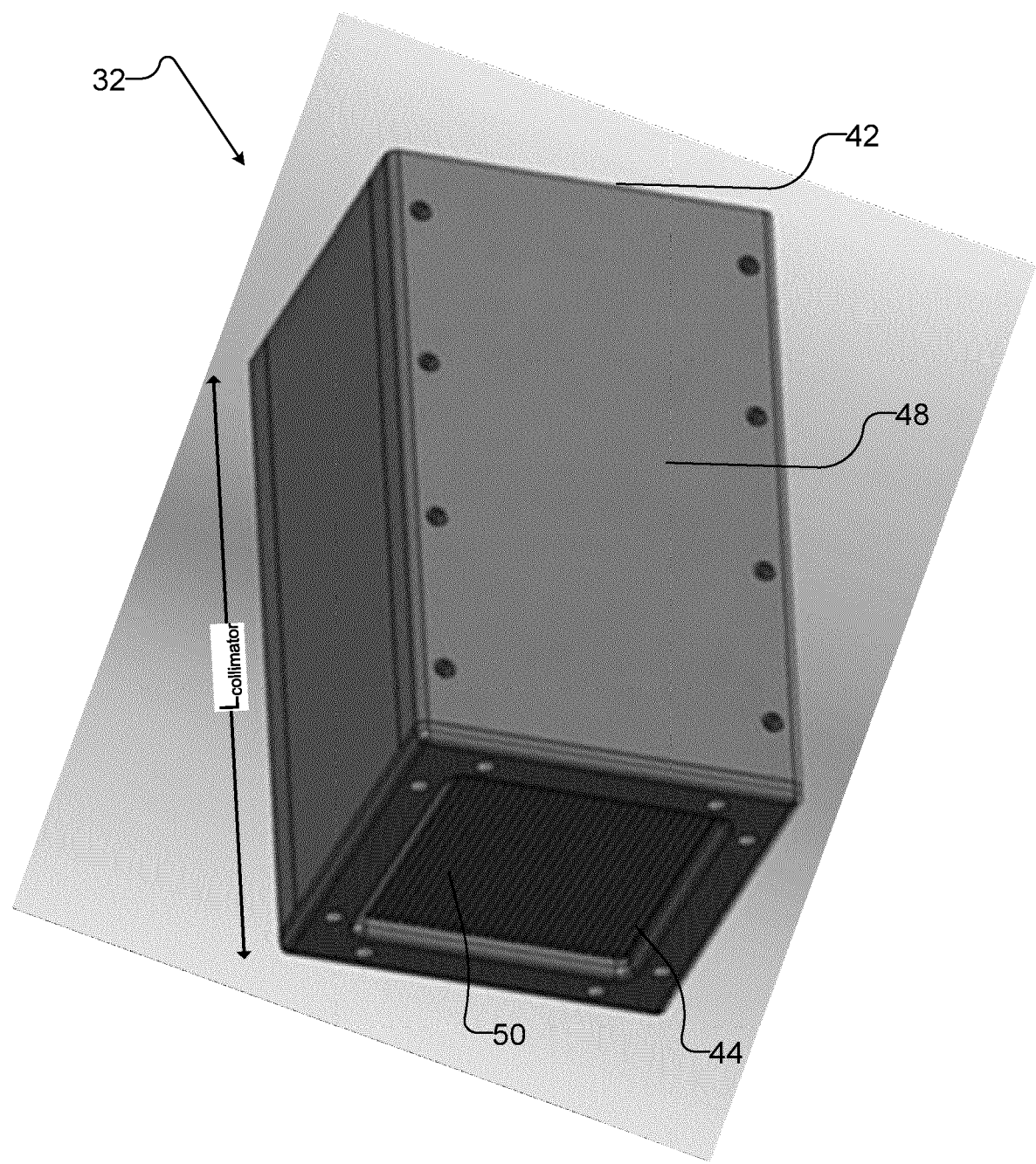
FIG. 4 is a perspective view of a mini-beam collimator according to a particular example embodiment.

FIG. 4 is a perspective view of an exemplary mini-beam collimator 32 according to an embodiment of this invention. Mini-beam collimator 32 comprises an input end 42 and an output end 44 at a side opposite to input end 42. Mini-beam collimator 32 is mounted to treatment head 26 or otherwise oriented such that open radiation beam 24 generated by linear accelerator 22 impinges on input end 42 of mini-beam collimator 32. Upon propagating through a length of mini-beam collimator 32, an output beam 34 having a spatially fractionated mini-beam dose profile exhibiting a peak and valley dose distribution pattern exits from output end 44 of mini-beam collimator 32. Output beam 34 is delivered to a subject S that is positioned in the path of output beam 34.

In the illustrated embodiments, collimator 32 comprises a housing 48. Housing 48 is sized and shaped to receive a plurality of collimator blades 50 that are spaced apart from each other by air gaps 52. In some embodiments, housing 48 comprises a rectangular cuboid-shaped configuration having a length in the range of approximately 50 to 300 mm and width and height in the range of approximately 30 to 150 mm. In general, however, housing 48 may be of any suitable size depending, for example, on the desired size of the entrance and exit apertures 53A,53B.

Figure 5A:
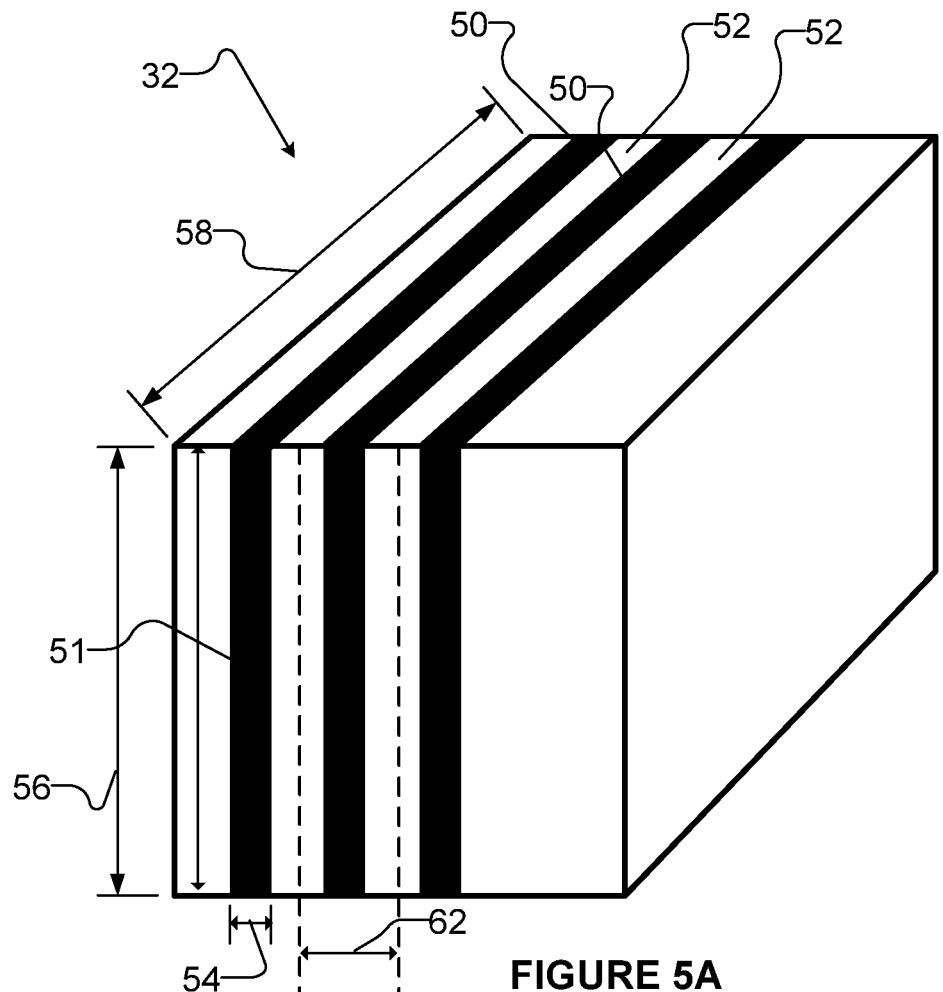
FIG. 5A is an isolated schematic view of the blades inside the FIG. 4 mini-beam collimator.

As best illustrated in FIG. 5A, each blade 50 may be characterized by blade width 54, blade height 56 and blade length 58. Blade width 54 and blade height 56 are the dimensions of blade 50 that are generally transverse to the direction of propagation of the center of open radiation beam 24. Blade length 58 is the dimension of blade 50 that is generally parallel to the direction of propagation of the center of open radiation beam 24. The surfaces 51 of collimator blades 50 are generally planar and blades 50 are spaced apart from one another to provide air gaps 52 between adjacent pairs of blades 50.

In some embodiments, blade width 54 is in a range of 0.4 mm-6 mm. In some embodiments, blade width 54 is in a range of 0.5 mm-2.5 mm. In some embodiments, blade width 54 is in a range of 0.6-1.0 mm.

In some embodiments, blade length 56 is in a range of 1 cm-25 cm. In some embodiments, blade length 56 is in a range of 2.0 cm-10 cm.

Figure 5B:
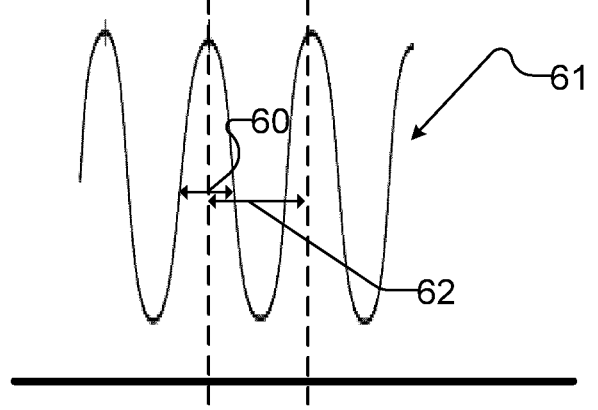
FIG. 5B schematically depicts an exemplary dose profile of an array of output mini-beams generated using the FIG. 4 mini-beam collimator.

FIG. 5B depicts a portion of an exemplary mini-beam dose profile 61, illustrating the relationship between blades 50, air gaps 52 and spatial fractionated radiation mini-beam dose profile 61. Gaps 52 permit the transmission of radiation through the collimator 32, whereas blades 50 are fabricated from materials which do not transmit radiation. Considering output beam 34 just after it exits from output end 44 of collimator 32, dose profile 61 of output beam 34 may comprise low 'valley' doses at locations corresponding generally to the locations of blades 50 and high 'peak' doses at locations corresponding generally to the locations of air gaps 52. At output end 44 of collimator 32, the beam width 60 of an individual mini-beam may be approximately equal to the width of air gaps 52. One skilled in the art will appreciate that output beam 34 emitted from collimator 32 will tend to diverge as it travels away from collimator 32. The transverse spread of output beam 34 increases with the distance from collimator 32. As a result, the beam widths 60 of individual mini-beams and peak-to-peak separation distances 62 of adjacent pairs of individual mini-beams in output beam 34 may be smaller when measured near output end 44 of collimator 32, as compared to at isocenter 40.

As shown in FIG. 6, a transverse width $W_{ai}$ of an entrance aperture 53A at input end 42 of collimator 32 is less than a transverse width $W_{ao}$ of an exit aperture 53B at output end 44 of collimator 32. To provide a gradual change in transverse width between $W_{ai}$ at entrance aperture 53A and $W_{ao}$ at exit aperture 53B, blades 50 are oriented at an angle relative to a central axis 64 of collimator 32 (which is aligned with a central axis 66 of open radiation beam 24. The angles at which blades 50 are oriented (relative to collimator axis 64) may depend on a divergence angle ($\theta$) of open radiation beam 24 (e.g. as emitted from internal collimators 28, 30). The two blades 50 that are positioned furthest away from the central axis 64 of collimator 32 may be referred to as blades $50_L$ and $50_R$. Blades 50L and 50R may be oriented (relative to central axis 64 of collimator 32) at angles that are equal to or near-equal to the divergence angle (θ) of open radiation beam 24. The remaining blades 50 located between blades $50_L$ and $50_R$ may be oriented at evenly angularly spaced intervals between the orientations of blades 50L and 50R (i.e. at evenly angularly spaced angles between (−θ,+ θ)).

One skilled in the art will appreciate that the divergence angle (θ) of open radiation beam 24 is a function of the source of the open radiation beam 24. In some embodiments, divergence angle (θ) is greater than or equal to 2°. In some embodiments, divergence angle is (θ) is greater than or equal to 5° In some embodiments, divergence angle is (θ) is greater than or equal to 10°.

In some embodiments, the transverse width of air gaps 52 is the same as the blade width 54 of blades 50 at output end 44 of collimator 32. In such embodiments, the peak-to-peak separation of adjacent individual mini-beams in output radiation beam 34 (at least just after being emitted from exit aperture 53B) may be approximately equal to the valley to valley separation of adjacent individual mini-beams in output radiation beam 34. This is not necessary, however. The widths of air gaps 52 and the widths 54 of blades 50 may be different from one another, in which case the peak-to-peak separation of adjacent individual mini-beams in output radiation beam 34 (at least just after being emitted from exit aperture 53B) may be different from one another. Thus, one skilled in the art will appreciate that peak-to-peak and valley-to-valley separation of adjacent individual mini-beams in output beam 34 (and the corresponding beam widths of the individual mini-beams) can be manipulated by changing the relative widths 54 of collimator blades 50 and air gaps 52. In some embodiments, the transverse widths of particular air gaps 52 may be different than the transverse widths of other air gaps 52 and/or the blade width 54 of particular blades 50 may be different than the blade width 54 of other blades 50.

In some embodiments, the transverse width of air gaps 52 is in a range of approximately 0.25 mm-1.25 mm. In some embodiments, the transverse width of air gaps 52 is in a range of approximately 0.35 mm-0.75 mm. In some embodiments, the transverse width of air gaps 52 is in a range of approximately 0.4 mm-0.65 mm.

In some embodiments, collimator 32 comprises an even number of blades 50 which are evenly angularly spaced apart from one another as discussed above. Providing collimator 32 with an even number of evenly angularly spaced blades 50 ensures that the central axis 64 of collimator 32 (which is aligned with a central axis 66 of open radiation beam 24) is coincident with an air gap 52. This would result in a mini-beam geometry that produces a central dose peak 16 along central beam axis 66 (or a central dose peak 16 at the radiation isocenter 40).

Figure 7A:
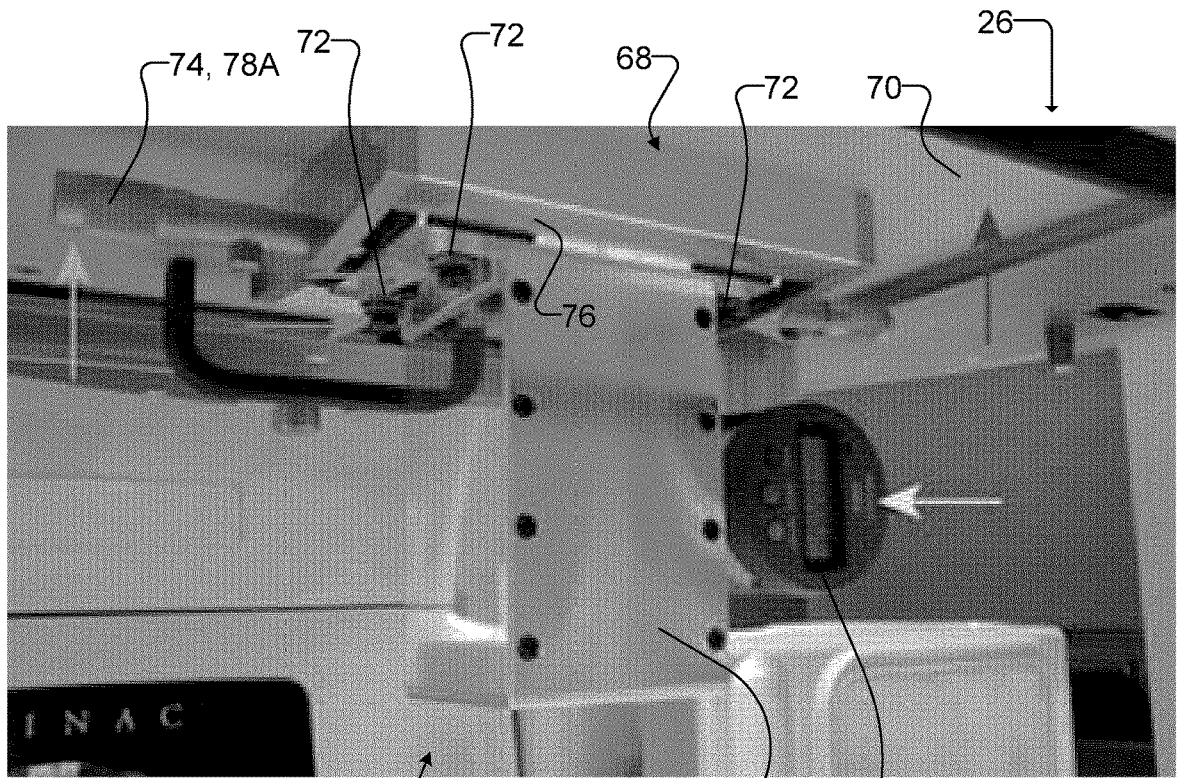
FIGS. 7A and 7B are photos showing the FIG. 4 mini-beam collimator mounted onto a medical linear accelerator.
Figure 7B:
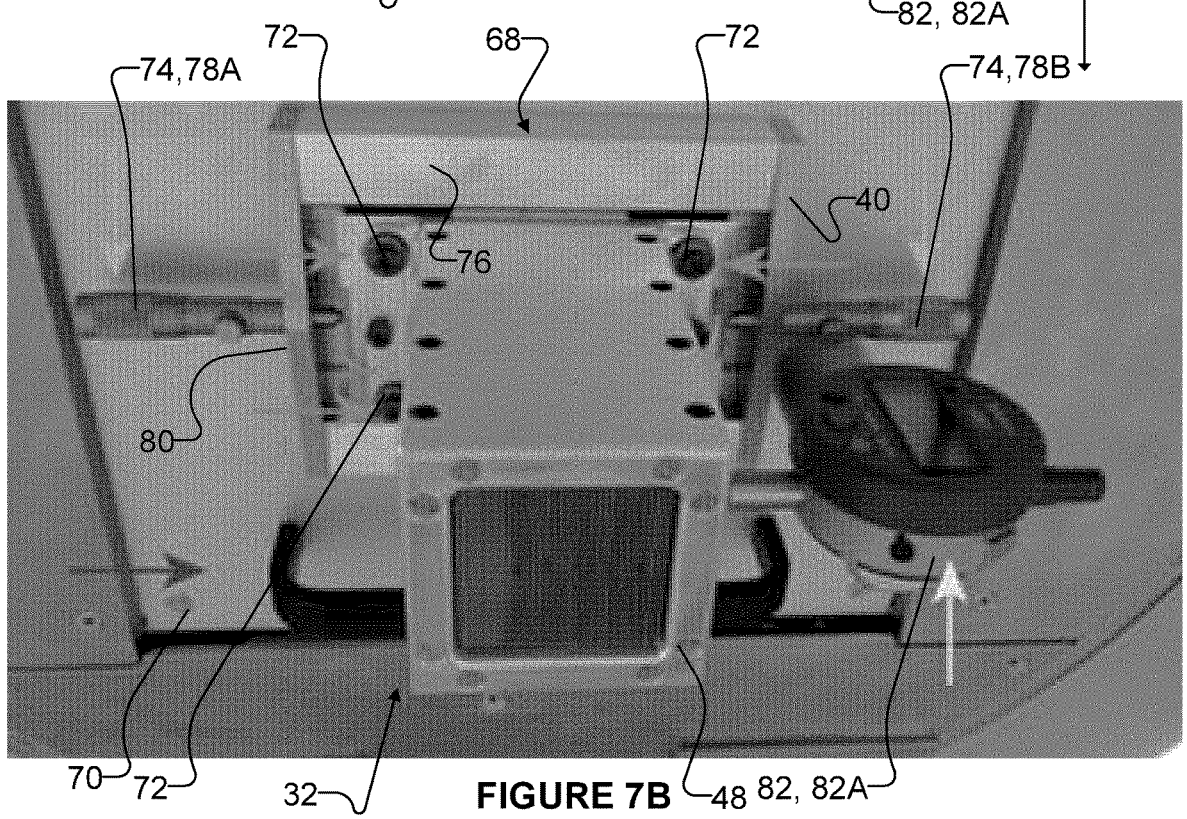

FIGS. 7A and 7B are close-up views of the attachment of mini-beam collimator 32 to treatment head 26 of a linear accelerator. Mini-beam collimator 32 may be mounted on or otherwise retrofitted onto a commercially available medical linear accelerator, such as, by way of non-limiting example, a Varian iX linear accelerator. This is not mandatory, however. Any suitable medical linear accelerator may be used. Medical linear accelerators are convenient because many treatment facilities are already equipped with medical linear accelerators, but the invention is not expressly limited to linear accelerators. In some embodiments, other radiation sources producing radiation beams of suitably high energies (e.g. in a range between 4 MV-25 MV or in any of the other ranges described herein) may be used in the place of a linear accelerator. In the illustrated embodiment of FIG. 7, mini-beam collimator 32 is affixed to the manufacturer supplied accessory tray 70 of the linear accelerator. In some embodiments, the input end 42 of collimator 32 is located at approximately 60 cm from the source (e.g. from the X-ray target in the linear accelerator).

In some embodiments, housing 48 of collimator 32 may be attached to a base plate 68. Base plate 68 may comprise a flat rectangular-shaped configuration for connecting collimator 32 to accessory tray 70 of linear accelerator 22.

Base plate 68 may comprise adjustment mechanisms 72, 74 for enabling precise control over the position of collimator 32 relative to accelerator head 26. Adjustment mechanisms 72, 74 may be used to ensure precise alignment of central collimator axis 64 with central beam axis 66. In the illustrated embodiment, base plate 68 comprises a set of angular adjustment mechanisms 72 and a set of lateral adjustment mechanisms 74.

Angular adjustment mechanisms 72 allow precise control over the angle of the collimator 32 relative to base plate 68 (and relative to linear accelerator 22 and its beam axis 66). Angular adjustment mechanisms 72 may comprise a plurality (e.g. four in the illustrated embodiment) of spring-loaded screws on a face 76 of base plate 68. In the illustrated embodiment of FIG. 7, a set of two spring-loaded screws is positioned at each lateral side of housing 48. Lateral adjustment mechanisms 74 allow precise control of the transverse location of collimator 32 relative to base plate 68 (and relative to linear accelerator 22 and its beam axis 66). Lateral adjustment mechanisms 74 may comprise a plurality (e.g. two in the illustrated embodiment) of micrometers 78A, 78B affixed to opposing lateral sides 80 of base plate 68. Lateral adjustment mechanisms 74 allow precise control over the lateral position of collimator 32 relative to base plate 68 (and relative to linear accelerator 22 and its beam axis 66).

A position sensing system 82 having a suitable output mechanism (e.g. display 82A) may be optionally provided. Position sensing system 82 may comprise one or more of any suitable radiation sensors and/or any suitable position sensors (not visible in FIG. 7) and is operable to detect and output a radiation measurement indicative of the alignment of collimator axis 64 with beam axis 66 and/or a position measurement indicative of a position of collimator 32 relative to linear accelerator 22 (and correspondingly of collimator axis 64 relative to beam axis 66). The precision associated with position sensing system 82 provides very fine positional adjustments of collimator 32 relative to linear accelerator 22 and thereby facilitates alignment of beam axis 66 with collimator axis 64. In the FIG. 7 embodiment, the alignment control provided by position sensing system 82 and adjustment mechanisms 72, 74 is manually operated. In some embodiments, translational adjustment mechanism 82 is adjusted until a radiation measurement measured by position sensing system 82 is maximized and, thereafter, angular adjustment mechanisms are adjusted in a similar manner to maximize a radiation measurement measured by position sensing system 82. It will be appreciated, however, that with the feedback provided by position sensing system 82, this alignment process could be automated using a computer controlled positioning system comprising a suitable controller and suitable actuators.

The inventors have discovered that the same collimator used with various commercially available linear accelerators will result in different mini-beam dose profiles. More particularly, the inventors have found that the resultant PVDR can vary across different linear accelerators. It is hypothesized that such difference in PVDR is due to the different electron beam width associated with different linear accelerators. Adjustment mechanisms 72, 74 and position sensing system 82 may be used to optimize the alignment of collimator 32 and collimator axis 64 with beam axis 66 (i.e. making these axes 64, 66 co-axial) which the inventors have determined minimizes the difference in PVDR across different linear accelerators.

Fine adjustments may be made to collimator 32 and/or linear accelerator 22 to achieve a mini-beam dose profile that is useful for mini-beam radiation therapy (e.g., to obtain a desired PVDR ratio, a desired beam width for individual mini-beams (at isocenter 40) and a desired peak-to-peak separation for adjacent individual mini-beams (at isocenter 40). For example, in one embodiment, a mini-beam collimator 32 that is designed to be mounted on an accessory tray of a Varian iX linear accelerator 22 comprises a collimator blade width 54, blade height 56 and blade length 58 of approximately 0.06 cm, 2.0 cm, and 10.0 cm respectively These collimator parameters were used to attain a mini-beam dose profile having a beam width between individual mini-beams of 1.0 mm at isocenter 40 across a field size of 5.0 cm×5.0 cm at isocenter 40.

Example

A mini-beam collimator in the form of collimator 32 described above comprising a collimator blade width 54, blade height 56 and blade length 58 of approximately 0.06 cm, 2.0 cm, and 10.0 cm respectively was mounted on an accessory tray of a Varian iX linear accelerator. To determine the effectiveness of mini-beam radiation therapy, canines with brain tumors were irradiated with a beam comprising an array of mini-beams created using a mini-beam collimator 32, as described above in a single fraction of 30 Gy. Control canine subjects were treated with stereotactic radiosurgery (SRS) in three fractions, each of 9 Gy, for a total of 27 Gy. Stereotactic radiosurgery is routinely and traditionally used to treat brain tumors by precisely delivering a single, high dose of radiation to the tumor volume.

Figure 8A:
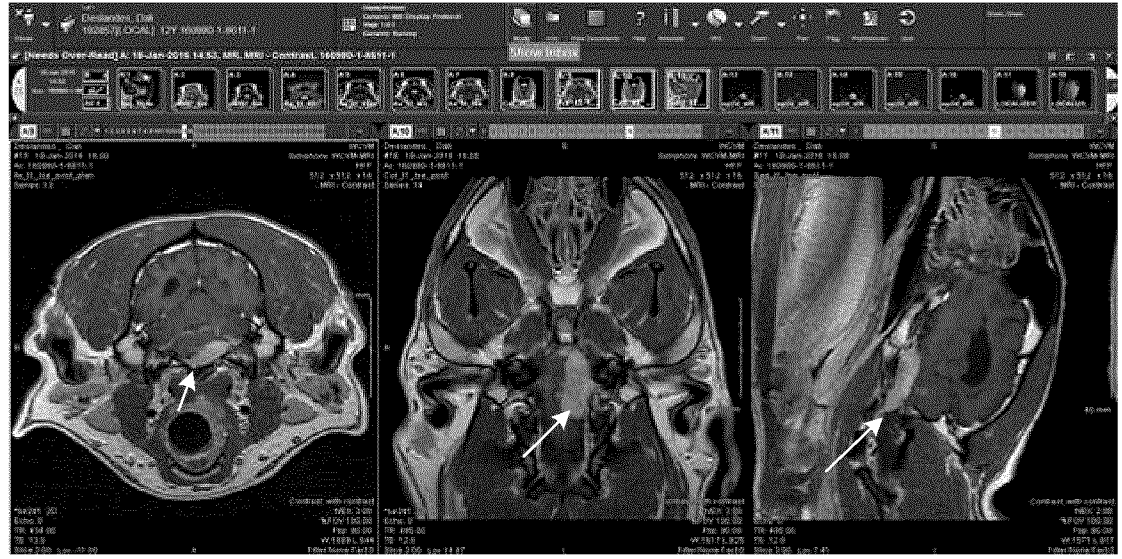
FIG. 8A is a MRI image of the brain of a first canine subject before receiving mini-beam radiation therapy created using a medical linear accelerator together with the FIG. 4 mini-beam collimator.
Figure 8B:
FIG. 8B is a MRI image of the brain of the first canine subject approximately five months after receiving mini-beam radiation therapy created using a medical linear accelerator together with the FIG. 4 mini-beam collimator.
Figure 9A:
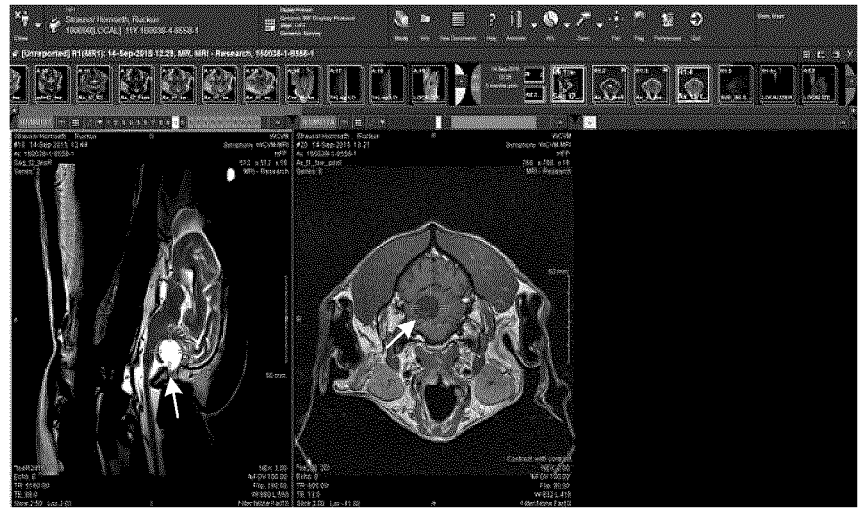
FIG. 9A is a MRI image of the brain of a second canine subject before receiving mini-beam radiation therapy created using a medical linear accelerator together with the FIG. 4 mini-beam collimator.
Figure 9B:
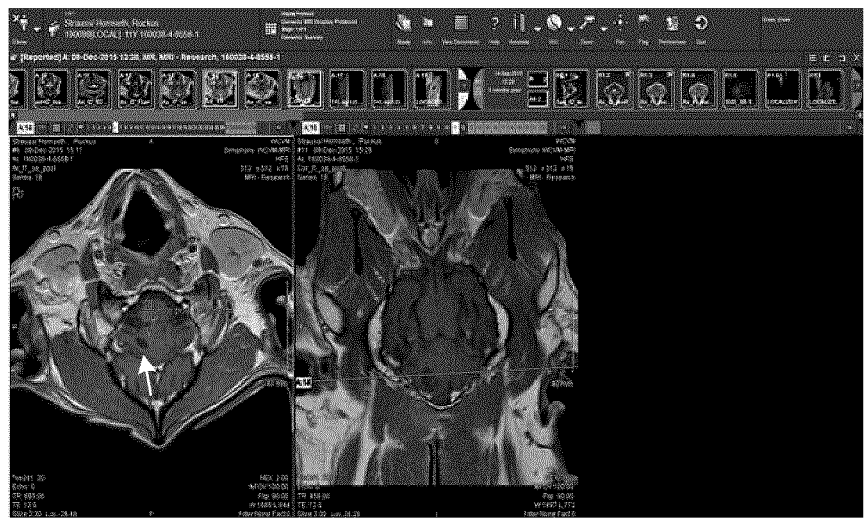
FIG. 9B is a MRI image of the brain of the second canine subject approximately three months after receiving mini-beam radiation therapy created using a medical linear accelerator together with the FIG. 4 mini-beam collimator.
Figure 9C:
FIG. 9C is a MRI image of the brain of the second canine subject approximately nine months after receiving mini-beam radiation therapy created using a medical linear accelerator together with the FIG. 4 mini-beam collimator.

FIGS. 8 and 9 are MRI images of the brains of two canine subjects before and after receiving mini-beam radiation therapy. FIG. 8A is an image taken before treatment and FIG. 8B is an image taken approximately five months after treatment. White arrows are used to point to the region of the tumor. Compared to the pre-treatment image (FIG. 8A), the post-treatment image (FIG. 8B) clearly shows that the tumor has disappeared within about five months after the subject was irradiated with mini-beams created by the mini-beam collimator 32 mounted on a Varian iX linear accelerator. Similarly, FIG. 9A is an image taken before treatment, FIG. 9B is an image taken about three months after treatment, and FIG. 9C is an image taken about nine months after treatment. While the tumor of the second canine subject is still visible post-treatment, the size of the tumor has noticeably reduced about three months after treatment (FIG. 9B). The reduced tumor was maintained about nine months after treatment (FIG. 9C).

Figure 10A:
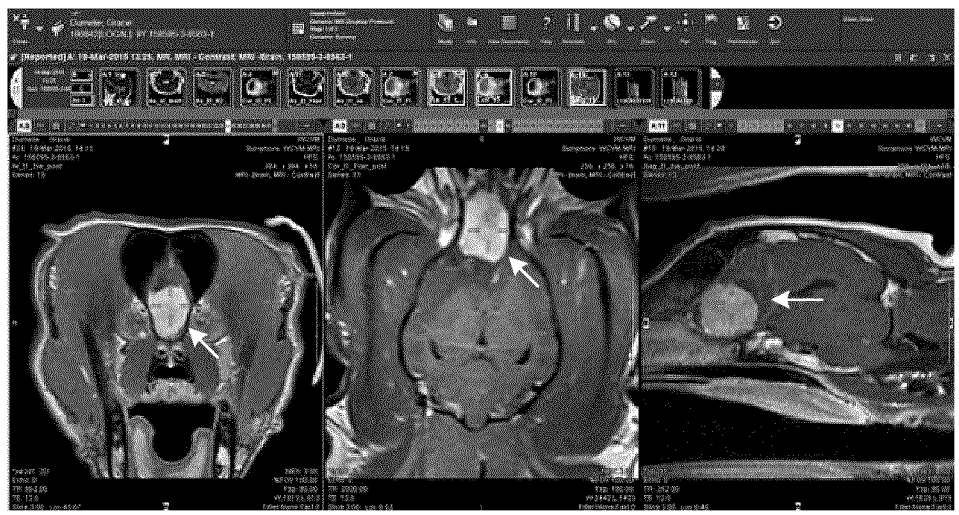
FIG. 10A is a MRI image of the brain of a canine control subject before receiving stereotactic radiation therapy.
Figure 10B:
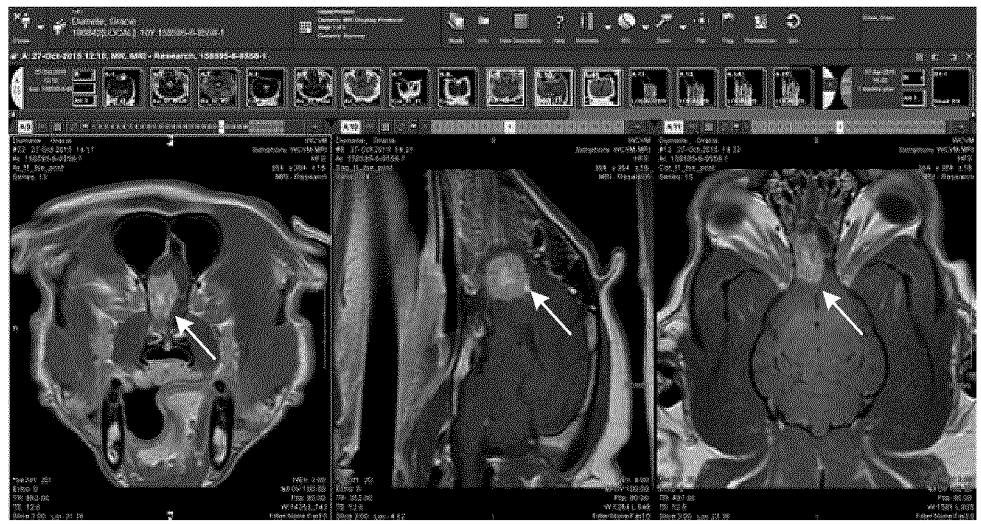
FIG. 10B is a MRI image of the brain of the canine control subject approximately six months after receiving stereotactic radiation therapy.
Figure 10C:
FIG. 10C is a MRI image of the brain of the canine control subject approximately twelve months after receiving stereotactic radiation therapy.

FIG. 10 illustrates MRI images of the brain of one control canine subject before and after receiving stereotactic radiation therapy. FIG. 10A is an image taken before treatment, FIG. 10B is an image taken approximately six months after treatment and FIG. 10C is an image taken approximately twelve months after treatment. Contrast to the treatment group that received mini-beam radiation therapy, a large mass of residual tumor is still visible in the brain of the control canine six and twelve months after receiving stereotactic radiation therapy.

Another aspect of the invention relates to methods of designing, building, and experimentally characterizing a linear accelerator mounted mini-beam collimator. In some embodiments, Monte Carlo simulation was used in the design and dosimetric characterization of a mini-beam collimator assembly.

Figure 11:
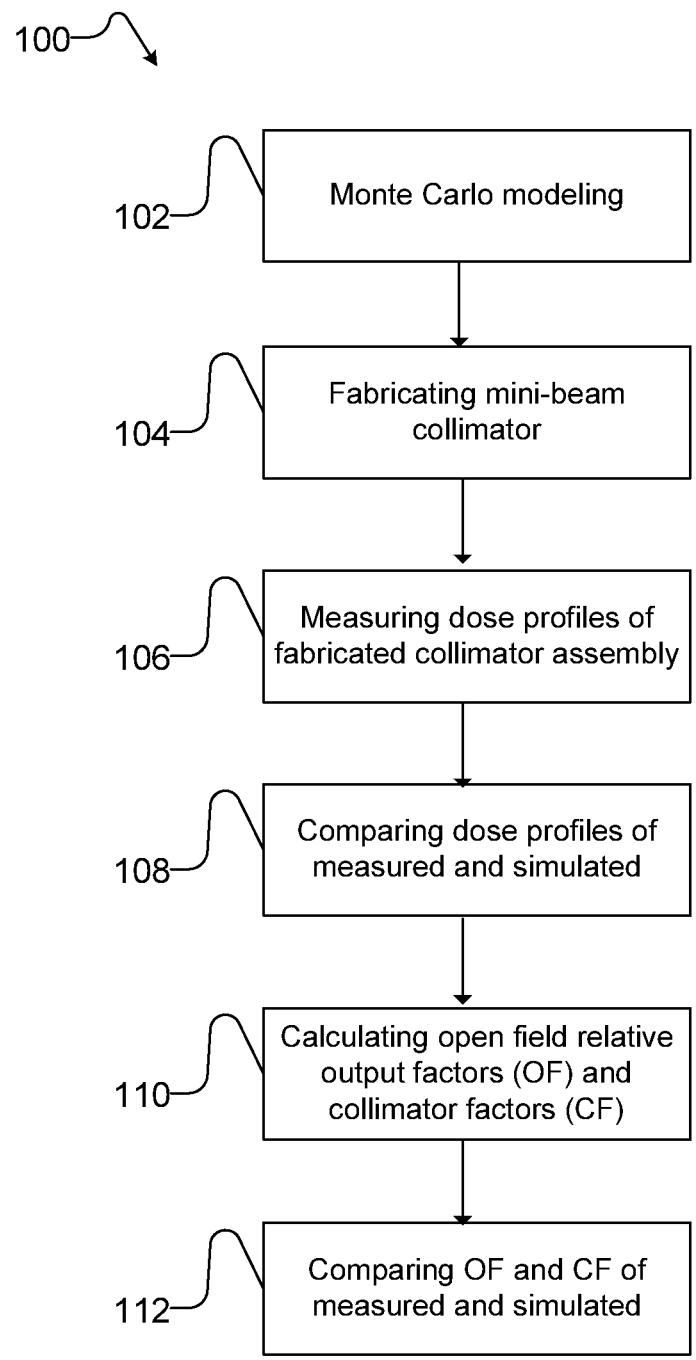
FIG. 11 is a flow chart illustrating a method for designing and experimentally characterizing a linear accelerator mounted mini-beam collimator according to an example embodiment of this invention.

FIG. 11 is a flow chart illustrating a method for designing and experimentally characterizing a linear accelerator mounted mini-beam collimator (or a mini-beam collimator mounted to a different radiation source of high energy photons, e.g. photon energies over 1 MV in some embodiments and over 4 MV in some embodiments) according to an example embodiment of this invention. Method 100 comprises creating and setting up models for Monte Carlo simulations (step 102). In some embodiments, the entire geometry, including the collimator, the linear accelerator and the water phantom was simulated. Step 102 involves optimizing the parameters of the collimator assembly (for example, by varying the collimator blade lengths and widths of the collimator and simulating the various conditions to determine the 'optimal' collimator blade dimension). The 'optimal' collimator blade dimension may be the blade length and width which would generate a mini-beam dose profile having the desired PVDR (e.g. a PVDR over a desired threshold). In some embodiments, the Monte Carlo code, BEAMnrc, may be used to model approximately 6 MV photon beams from Varian iX medical linear accelerator. In some embodiments, the ARCCHM component module may be used to model a mini-beam collimator. In some embodiments, the Monte Carlo code, DOSXYZnrc simulations may be used to model a water phantom. Monte Carlo simulated dose profiles may be generated in step 102 (see for example, FIG. 12).

Figure 6B:
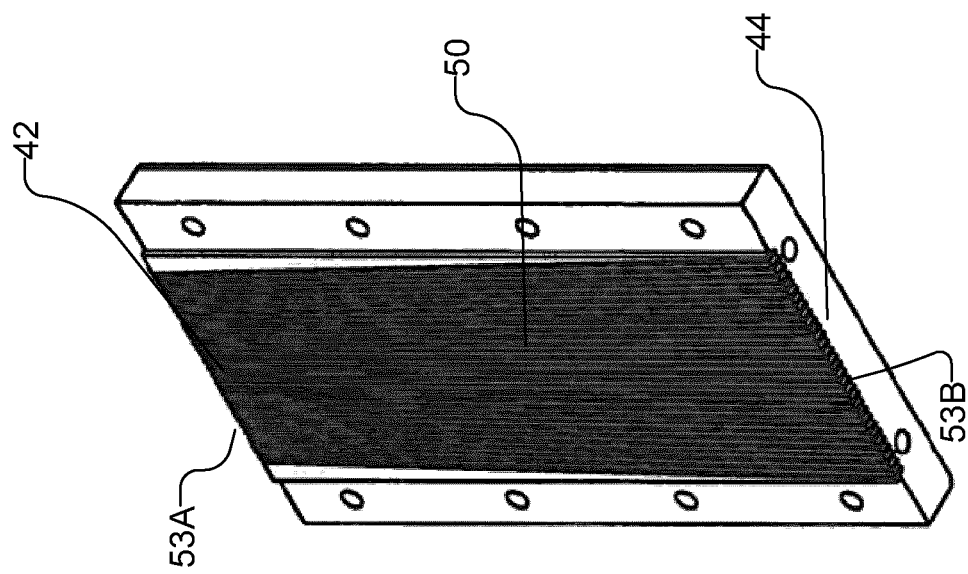
FIG. 6A is a sectional view and FIG. 6B is a sectional perspective view of the FIG. 4 mini-beam collimator showing the inside of the collimator.
Figure 6A:
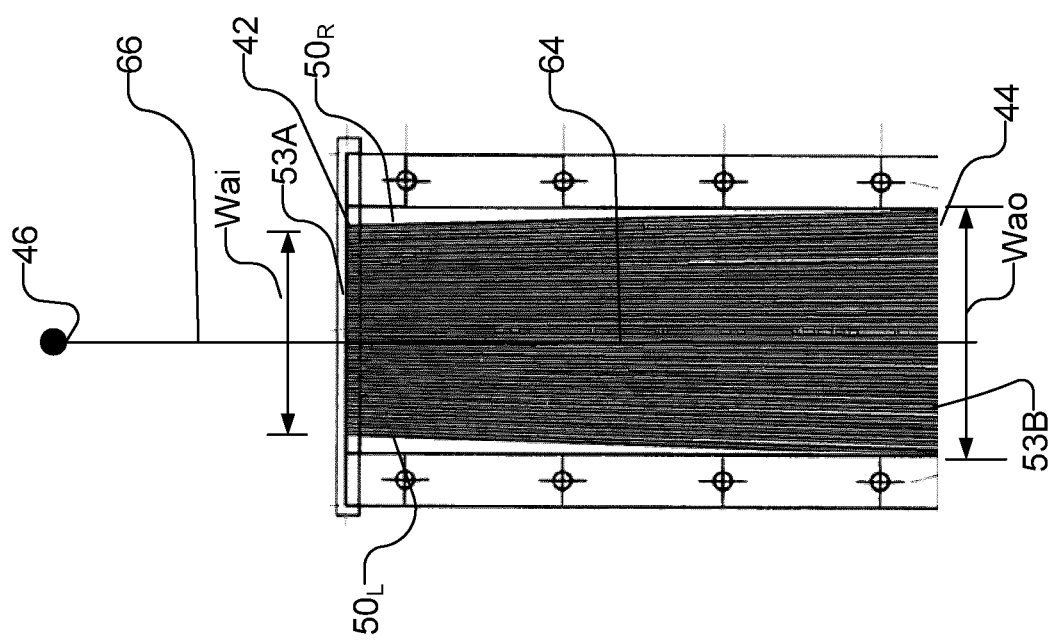

Step 104 involves fabricating a mini-beam collimator 32 based on the results of step 102. For example, a collimator 32 comprising the 'optimal' blade dimensions as determined in step 102 would be built. An example collimator 32 that is fabricated using step 102 is shown in FIGS. 4, 6A and 6B. The collimator 32 is then mounted on a head of a linear accelerator, as shown in FIGS. 7A and 7B.

Step 106 comprises measuring the mini-beam dose profiles using the block 104 linear accelerator mounted mini-beam collimator 32. Step 108 comprises comparing the dose profiles generated in step 106 with the simulated profiles generated in step 102. This can be done by overlapping the block 106 measured mini-beam profiles with the block 102 Monte Carlo simulated dose profiles (see, for example, FIG. 14).

In order to demonstrate dosimetric traceability through a dosimetric code of practice for the fabricated medical linear accelerator mounted mini-beam collimator, the open field relative output factors (OF) and the collimator factors (CF) of the simulated and measured data are determined and compared (steps 110 and 112). Dosimetric traceability can be established if the calculated OF and CF of the block 106 measured data and of the block 102 simulated data are within an acceptable level of uncertainty required for dosimetric traceability of non-standard field geometries.

The following examples illustrate exemplary embodiments of method 100. The following examples are intended to be illustrative and not limiting in nature.

EXAMPLES

Example 1.0—Monte Carlo Modelling

Example 1.1—Linear Accelerator Head Simulations

A BEAMnrc (Rogers et al. 1995) model of a Varian iX medical linear accelerator head (Varian Medical Systems, Palo Alto, Calif.) (including the target, primary collimator, flattening filter, MU chamber, mirror, and collimator jaws) was used throughout this study (Babcock et al. 2008). The initial electron source parameters were as follows: 6.2 MeV mono-energetic with a circularly symmetric Gaussian FWHM (full width at half maximum)=0.110 cm. The electron FWHM was established through an evaluation of dose profiles and relative output for a set of very small field sizes (Cranmer-Sargison et al. 2011, Cranmer-Sargison et al. 2012, Cranmer-Sargison et al. 2013). The general simulation set-up used a fixed history number of $1.0 \times 10^9$ with directional Bremsstrahlung splitting (DBS) set at a maximum splitting number of 100. In all cases the EGSnrc transport parameters ECUT, PCUT and ESTEP were set to 0.700 MeV, 0.01 MeV and 0.25 respectively.

The general mini-beam collimator design was such that the front face (entrance aperture) of the collimator was to be located at 60 cm from the source with the array of collimator blades following the photon beam divergence ($\theta$) as discussed above. This geometry allowed for a compact collimator assembly which could be inserted into the interface mount ("Slot 1") on the Varian iX accelerator head. The collimator aperture dimensions were set to ensure a mini-beam dose distribution across a jaw collimated 5.0 cm×5.0 cm field size at isocenter. The mini-beam peaks were to be collimated using tungsten blades such that each peak dose was separated by a valley dose of equivalent width.

Example 1.1.2 Mini-Beam Collimator Simulations

A BEAMnrc collimator model was constructed using the ARCCHM component model. As outlined in the BEAMnrc user manual (Rogers et al. 2012), the ARCCHM component module can be used to model segmented arc-type structures in the beam path—such as a divergent mini-beam collimator. The ARCCHM geometry consists of a series of "chamber elements" separated by "septa", all within the chamber front and back faces. The distance between the front face and the source is specified using the variable ZSRC, with the front face radius specified using ZRAD1. The media and transport parameters (ECUT, PCUT) can be set independently for each region or in a repeating fashion.

The general mini-beam collimator model comprised a series of tungsten "blades" separated by air "septa" all within a front and back face of air. Using an even number of blades ensured the beam central axis was coincidence with the center septa, which results in a collimator geometry that produces a dose peak along the central beam axis. In all cases ZSRC=ZRAD1 at 60 cm from the Bremsstrahlung target. The model was run as a standalone simulation using a phase space (PHSP) file as input. The input PHSP was scored directly below the collimator jaws. EXACT Boundary crossing algorithm was employed as was the PRESTA-II electron-step algorithm. The transport parameters ECUT, PCUT and ESTEP were set to 0.700 MeV, 0.01 MeV and 0.25 respectively. Valley-to-peak dose ratios (VPDR) were evaluated for varied blade widths of between 0.3 mm and 1.0 mm (incremented in steps of 0.1 mm) and varied blade lengths between 2.0 cm and 10.0 cm (incremented as follows: 2.0, 4.0, 5.0, 6.0 and 10.0).

Example 1.1.3—Water Phantom Simulations

DOSXYZnrc simulations were used to model a water phantom measuring 10 cm×10 cm×10 cm. The history number for each simulation was set to $5.0 \times 10^8$, which resulted in a statistical uncertainty of less than ±0.5% within a voxel dimension of 0.01 cm×0.05 cm×0.1 cm. In all cases the EGSnrc transport parameters ECUT, PCUT and ESTEP were set to 0.700 MeV, 0.01 MeV and 0.25 respectively. Dose profile data across the mini-beam axis was extracted for each blade width and length combination and used in the VPDR analysis.

Example 1.2—Mini-Beam Collimator Fabrication

A tungsten blade length and width of 10.0 cm and 0.6 mm was selected to meet the underlying design constraint of a maximum 1.0 mm wide peak dose at isocenter, while attaining the lowest possible valley-to-peak dose ratio. Fabrication drawings were developed using the SolidWorks software environment (Dassault Systemes SolidWorks Corporation, Waltham, Mass.) and prefabrication renderings reviewed to ensure the box used to hold the tungsten blades produced a collimator blade divergence angle consistent with the actual beam divergence.

Example 1.3—Dosimetric Characterization

All experimental work was performed using a Varian iX linear accelerator at a nominal beam energy of 6 MV. The linear accelerator was commissioned for clinical radiotherapy use and subject to routine performance testing which followed the American Association of Physicists in Medicine (AAPM) TG-142 recommendations (Klein et al. 2009). The AAPM TG-51 (Almond et al. 1999) reference dosimetry formalism was used to calibrate the 6 MV photon beam of quality % $dd_{10\ cm}$=0.67. The LINAC output was calibrated to produce 1.00 cGy·MU$^{-1}$ at $d_{max}$ for a square field size of side 10 cm using an SSD=100 cm set-up.

Example 1.3.1—Mini-Beam Dose Profile Measurements

Dose profiles were measured using the stereotactic field diode (SFD) (IBA Dosimetry, Bartlett, Tenn.) positioned using a MP3 scanning water tank (SSD=100 cm) (PTW-New York Corporation, Brooklyn, N.Y.). To maximize the spatial resolution the detector was placed horizontal to the central beam axis (Beddar et al. 1994) and perpendicular to the peak-and-valley dose distribution. The profile step size was set to 0.2 mm, which is twice the quoted positional uncertainty of the water tank system itself. Positional fine tuning of the detector zero coordinate was performed prior to mini-beam profile measurements. This procedure was adopted from dosimetry work performed for very small MV photon beams (Cranmer-Sargison et al. 2013, Charles et al. 2014) and ensured the zero coordinate of the detector active volume was aligned with the radiation isocenter. Fine tuning of the mini-beam collimator was then performed using the lateral micrometer adjustment mechanism. This ensured the central mini-beam peak dose was aligned with the detector active volume, which was already aligned with the radiation isocenter. Mini-beam profile measurements were performed at depths of 1.5, 5.0 and 10.0 cm for a square field size of side 4.0 cm.

Example 1.3.2—Open Field Relative Output

The standard clinical practice for determining the absorbed dose to water is to follow a code of practice (CoP). Two such CoPs are the American Association of Physicists in Medicine (AAPM) Task Group Report 51 (TG-51) (Almond et al. 1999) and the International Atomic Energy Agency (IAEA) Technical Report Series No. 398 (Andreo 2000). Following a code of practice (CoP) to establish the absorbed dose to water at a point is generally referred to as reference dosimetry. The dose associated with all other beam configurations can then be reported as relative values with respect to the reference conditions. One very common example of relative dosimetry is measuring and reporting the change in dose as a function of the change in field size.

Output factors (OF) are typically defined as clinical field size specific ($f_{clin}$) relative point dose (D) ratios in water (w) taken with respect to a machine specific reference field ($f_{msr}$). In non-standard dosimetry applications a machine specific reference field is typically used as an intermediary field size between that of the CoP reference field ($f_{ref}$) and the clinical field size of interest, such that, $$OF^w_{f_{clin}} = \frac{D^w_{f_{clin}}}{D^w_{f_{msr}}}. \quad [1]$$

Under Bragg-Gray conditions, which imply charge particle equilibrium (CPE) and that the insertion of a Bragg-Gray cavity (i.e. ionization chamber) is assumed not to perturb the CPE, output factors can generally be considered equivalent to the ratio of ionization chamber (ion) readings (M) measured $$\frac{D^w_{f_{clin}}}{D^w_{f_{msr}}} = \frac{M^{ion}_{f_{clin}}}{M^{ion}_{f_{msr}}}. \quad [2]$$

It may be noted that Eq. [2] only applies where the combination of field size, detector selection and position are such that CPE is not compromised (Das et al. 2008). The accuracy associated with output factor measurements made with different types of detectors (det) can be validated by comparing the ratio of readings. In short, one would validate the following, $$\frac{M^{ion}_{f_{clin}}}{M^{ion}_{f_{msr}}} = \frac{M^{det}_{f_{clin}}}{M^{det}_{f_{msr}}}. \quad [3]$$

Example 1.3.3—Experimental Open Field Relative Outputs

A comparison of central axis relative output factors was performed for square field sizes of side 2.0, 3.0 and 4.0 cm with respect to a square, machine specific, reference field of side 5.0 cm (d=10 cm and SSD=100 cm). The comparison data comprised experimental measurement, LINAC commissioning data as well as Monte Carlo simulation results. The experimental data was measured using an ionization chamber (CC04) (IBA Dosimetry, Bartlett, Tenn.), the stereotactic field diode (SFD) and the T60017 electron diode detector ($PTW_e$) (PTW-New York Corporation, Brooklyn, N.Y.).

The ionization chamber orientation was such that the long axis of the detector was placed perpendicular to the central beam axis, with the detector active volume aligned with the radiation isocenter. The diode detector orientation was such that the long axis of the detector was placed parallel to the central beam axis, with the detector active volume aligned with the radiation isocenter. Measurements were repeated three times with the water phantom, detector position and jaw/collimator reset between each experimental session. Five readings were taken for each field size during each experimental session. For each field size the standard error on the mean relative output was less than ±1.0% (Cranmer-Sargison et al. 2011a).

Example 1.3.4—Monte Carlo Simulated Open Field Relative Outputs

Monte Carlo simulation of the SFD and $PTW_e$ diode detectors was performed as follows. For each field size a PHSP file was scored below the LINC jaws. Each PHSP file was then used as input into a DOSRZnrc simulation of the SFD and $PTW_e$ detector as well as an equivalent all water geometry (Cranmer-Sargison et al. 2011b). The active volume radius was 0.300 mm within a chip radius of 0.500 mm for the SFD and 0.0564 mm within a chip radius of 0.750 mm for the $PTW_e$. The simulated output ratio was calculated for each detector using the following, $$OF^{det}_{f_{clin}} = \left(\frac{D^{det}_{f_{clin}}}{D^{det}_{f_{msr}}}\right)_{MC} \cdot \left(\frac{D^m_{f_{msr}}}{D^m_{f_{clin}}}\right)_{MC}. \quad [4]$$

$D_{f_{clin}}^{det}$, $D_{f_{msr}}^{det}$, $D_{f_{clin}}^{m}$ and $D_{f_{msr}}^{m}$ represent the dose per incident particle scored to the active volume of the detector model and LINAC monitor unit chamber for the $f_{clin}$ and $f_{msr}$ simulations respectively. Incorporating $$\left(\frac{D^m_{f_{msr}}}{D^m_{f_{clin}}}\right)_{MC}$$

into the output ratio calculation correctly accounts for the change in backscatter dose to the monitor chamber as a function of field size.

Example 1.3.5—Mini-Beam Relative Output

The field size specific relative output ratio for a mini-beam irradiation is defined here as the open field relative output in water multiplied be a collimator factor such that, $$OF^w_{f_{mini}} = OF^w_{f_{clin}} \times CF^w_{f_{mini}} \quad [5]$$

The collimator factor is defined as the ratio of point doses to water for the mini-beam collimated field relative to that of the open field geometry, such that, $$CF^w_{f_{mini}} = \frac{D^w_{f_{mini}}}{D^w_{f_{clin}}}. \quad [6]$$

In all cases the field size is assumed to be the same for both the mini-beam and clinical field size of interest. For example, a square $f_{mini}$ of side 4.0 cm implies a jaw collimated square $f_{clin}$ of side 4.0 cm but with the mini-beam collimator in the beam path.

In general, the ratio of point doses to water for the mini-beam geometry cannot be considered equivalent to the ratio of detector readings. However, the relative dose to detector can be considered equivalent to the ratio of detector readings and therefore an experimental, detector specific, collimator factor can be measured and reported as follows, $$CF_{f_{mini}}^{det} = \frac{D_{f_{mini}}^{det}}{D_{f_{clin}}^{det}} = \frac{M_{f_{mini}}^{det}}{M_{f_{clin}}^{det}}. \qquad [7]$$

Although the ratio in Eq. [7] can be measured, another factor must be applied to correct for differences in detector response in both fields relative to the actual point dose ratios in water. The measured collimator factor of Eq. [7] can be equated to the collimator factor of Eq. [6] by applying a detector specific correction factor to the measurement ratio, such that, $$CF_{f_{mini}}^{w} = CF_{f_{mini}}^{det} \times k_{f_{mini}}^{det} \qquad [8]$$

$k_{f_{mini}}^{det}$ is, in essence, the same as that proposed by Alfonso et al (2008) for traceability in small and non-standard field dosimetry applications, which can be calculated by Monte Carlo simulation alone. $k_{f_{mini}}^{det}$ can be calculated using Monte Carlo simulation results as follows, $$k_{f_{mini}}^{det} = \left[\frac{\left(\frac{D_{f_{mini}}^{w}}{D_{f_{clin}}^{w}}\right)}{\left(\frac{D_{f_{mini}}^{det}}{D_{f_{clin}}^{det}}\right)}\right]_{MC}, \qquad [9]$$

where, $D_{f_{mini}}^{w}$, $D_{f_{clin}}^{w}$, $D_{f_{mini}}^{det}$ and $D_{f_{clin}}^{det}$ represent Monte Carlo calculated dose (D) to water (w) or detector (det) for the open field size of interest ($f_{clin}$) and the associated mini-beam field ($f_{mini}$). As Alfonso et al. highlight, following just such a methodology can ensure dosimetric traceability back to a CoP for small and non-standard dosimetry conditions—mini-beam radiotherapy applications being a clear example of non-standard dosimetry conditions.

Example 2.1—Results of Mini-Beam Collimator Simulations

Example 2.1.1 Dose Profile Characteristics

Figure 12:
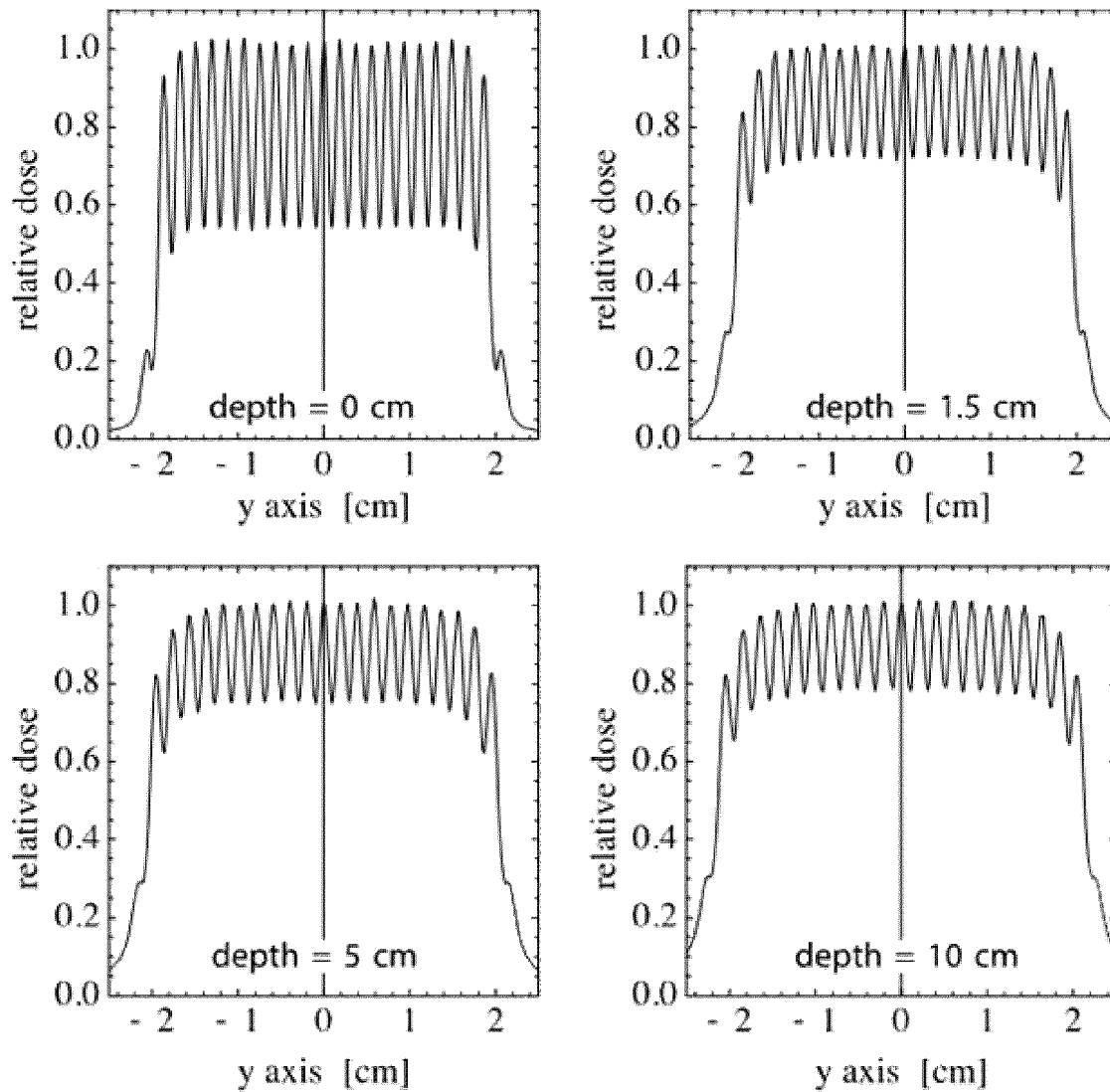
FIG. 12 shows Monte Carlo simulated dose profiles taken across the mini-beam axis.

A set of DOSXYZnrc calculated dose profiles are shown in FIG. 12. The blade width and inter-blade spacing were uniform at 0.5 mm with a blade length of 10.0 cm. The profiles are taken at the water phantom surface as well as depths of d=1.5, 5.0 and 10.0 cm. The data reveals a general characteristic—reduced VPDR as a function of depth in water. With a maximum 1.0 mm peak dose width at isocenter serving as an initial design constraint the lowest possible VPDR as a function of collimator blade became the focus of the characterization analysis.

Example 2.1.2—Valley-to Peak Dose Ratio

Figure 13A:
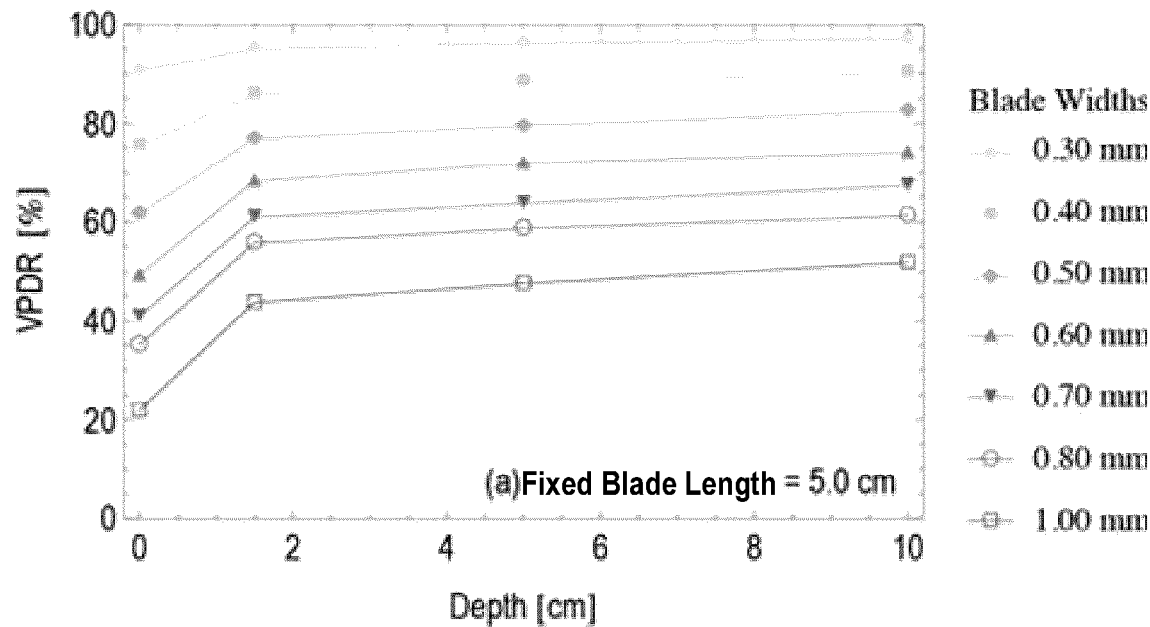
FIGS. 13A and 13B show valley-to-peak dose ratios (VPDRs) as a function of depth in water for various Monte Carlo simulated collimator geometries.
Figure 13B:
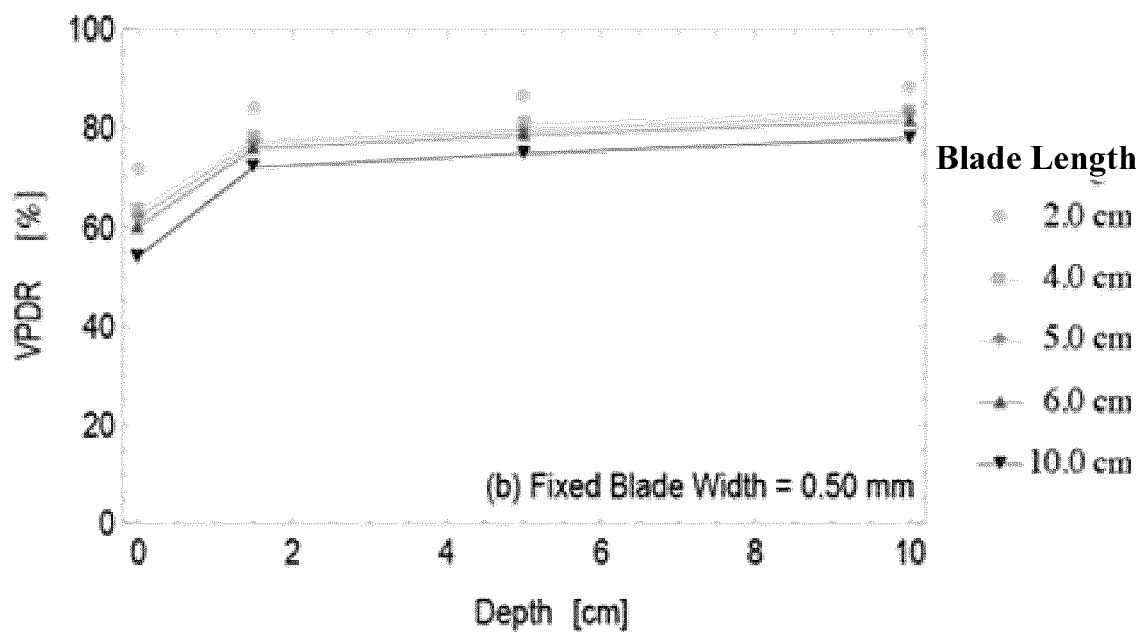

FIGS. 13A and 13B present VPDR data calculated using DOSXYZnrc dose profiles at depths of 0.0, 1.5, 5.0 and 10.0 cm. The VPDR was calculated as the average valley dose divided by the average peak dose presented as a percentage. The average values were calculated across all but the two outermost peaks and valleys. This was done to remove the beam penumbra as a compounding influence in the VPDR characterization. The first set of data characterizes the VPDR as a function of depth for a simulated mini-beam collimator with a fixed blade length of 5.0 cm and a set of blade widths that varied from 0.30 mm to 1.00 mm. The second set of data characterizes the VPDR as a function of depth for a simulated mini-beam collimator with a fixed blade width of 0.50 mm and a set of blade lengths that varied from 2.0 cm to 10.0 cm. The two data sets clearly show that changes in blade width have a greater influence on VPDR than do changes in blade length. Having quantified the influence of collimator blade dimension on VPDR the final blade width and length were chosen to be 0.6 mm and 10.0 cm respectively.

Example 2.2—Results of Mini-Beam Experimental Characterization

Example 2.2.1 Mini-Beam Dose Profile

Figure 14A:
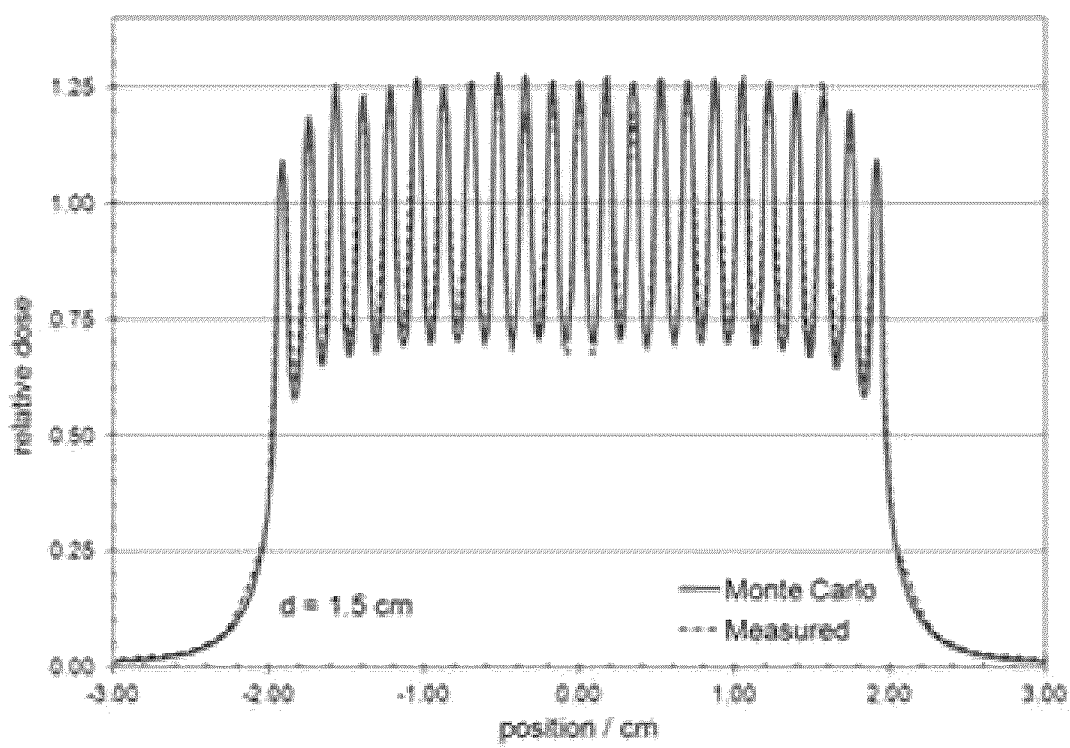
FIGS. 14A, 14B and 14C show measured and Monte Carlo simulated dose profiles.
Figure 14B:
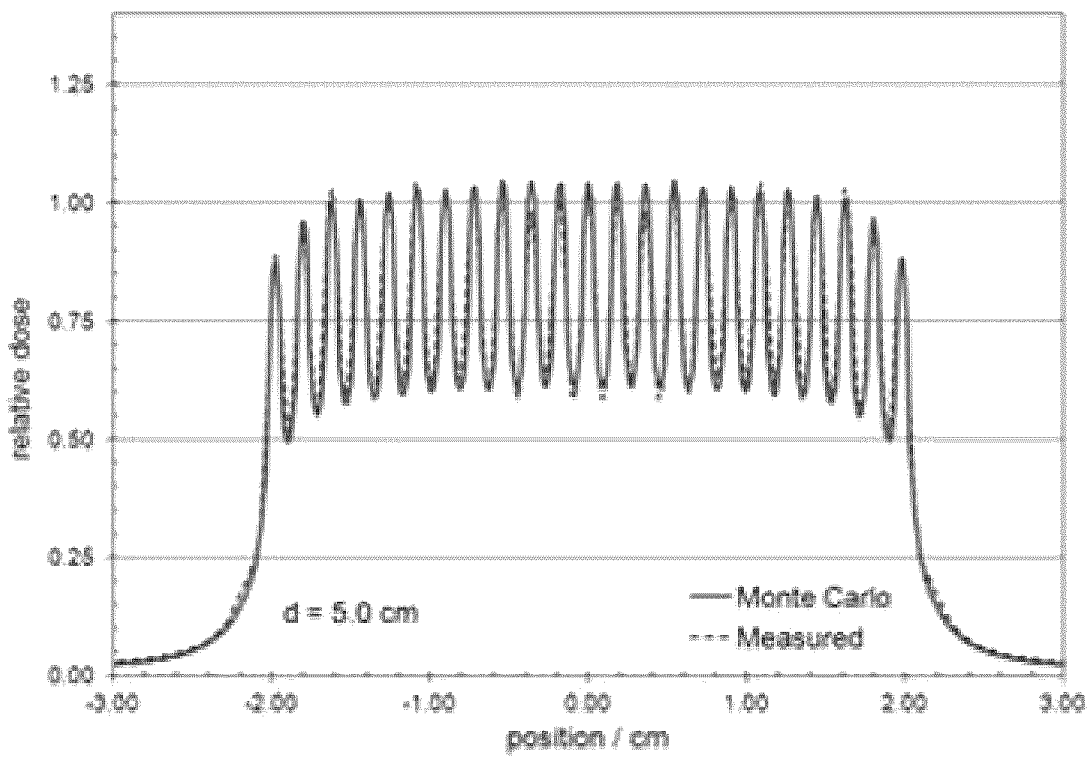
Figure 14C:
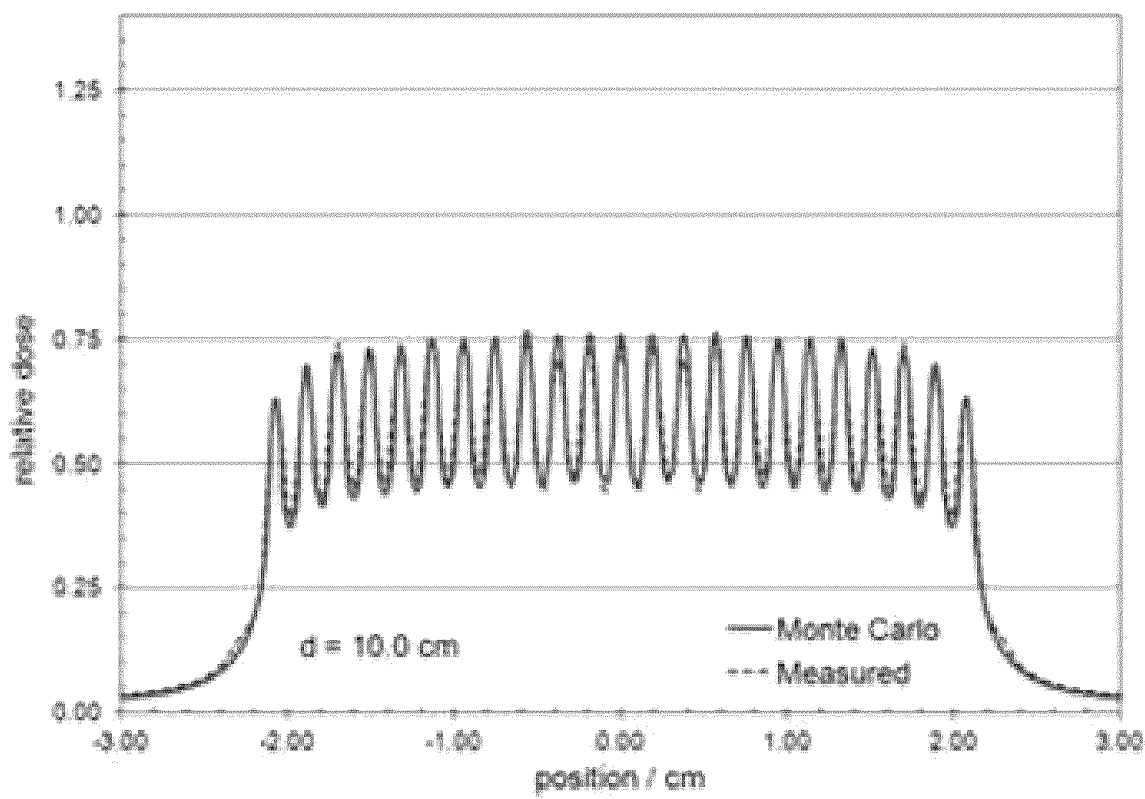

Shown in each of FIGS. 14A, 14B and 14C is a comparison between the experimentally measured mini-beam profile data and that of the associated DOSXYZnrc simulation data. The profile data was normalized using the 50% width of the central peak at a depth of 1.5 cm. The simulation data represents an "as built" collimator model and not that of the VPDR characterization model. The "as built" collimator model differed from the initial collimator geometry in that the top face of the collimator blades were located at 58.9 cm from the Bremsstrahlung target and not the initially desired 60.0 cm. A minor adjustment was also made to the spatial distribution of the electron source from the initial circularly symmetric Gaussian FWHM=0.11 cm to that of a final FWHM=0.09 cm.

With the physical dimensions and materials of both the LINAC and diode detectors well known the only free variable available to assist in fine tuning the model is the energy and spatial distribution of the electron source incident on the Bremsstrahlung target. Making this type of fine adjustment to the source width was not a surprise as indicated by recent work in Monte Carlo accelerator head model validation in small field dosimetry applications (Cranmer-Sargison et al. 2011, Cranmer-Sargison et al. 2013, and Francescon et al. 2011). There was good agreement between the modelled and measured data with the exception of the small differences on either side of the central peak. These differences were found to be systematic across all depths and are thought to result from limitations associated with the collimator fabrication. It would be within the expected ability of one skilled in the art to make further refinements in the fabrication process.

Example 2.2.2—Open Field Relative Output

Open field relative output factor data is shown in Table 1. The data set is comprised of experimental results measured using both ionization chamber (CC04) and diode detectors (SFD and PTW$_e$), clinical commissioning data, DOSRZnrc diode detector simulation data and a simulated all water geometry. Following the concepts associated with Eqs. [1] and [2] the output factors derived from the all water simulation geometry should be the same as the ionization chamber results. One can clearly see there is good agreement between all three data sets—good agreement defined as the percentage difference between measurement and simulation of less than ±1.0%. There is also good agreement between the measured and simulated diode detector results. This too was expected as these models had previously been commissioned for small field dosimetry applications (Cranmer-Sargison et al. 2011, Cranmer-Sargison et al. 2012).

TABLE 1

Measured and MC simulated open field relative output factor data.

| Field | Monte Carlo: $OF_{fclin}^{w}$ and $OF_{fclin}^{det}$ | | | Measured: $OF_{fclin}^{det}$ | | |
|---|---|---|---|---|---|---|
| Size | Water | SFD | PTWe | CC04 | SFD | PTW$_e$ |
| 5 × 5 | 1.000 | 1.000 | 1.000 | 1.000 | 1.000 | 1.000 |
| 4 × 4 | 0.968 | 0.963 | 0.964 | 0.968 | 0.961 | 0.964 |
| 3 × 3 | 0.932 | 0.922 | 0.928 | 0.930 | 0.918 | 0.923 |
| 2 × 2 | 0.887 | 0.879 | 0.883 | 0.884 | 0.870 | 0.879 |

Example 2.2.3—Mini-Beam Relative Output

Shown in Table 2 are the simulated and measured collimator factors as defined in Eqs. [5] and [6] respectively. The collimator factor of Eq. [6], which by definition is the ratio of point doses to water, is represented by the all water simulation data. The combined experimental and Monte Carlo percent uncertainty for the SFD and PTWe detectors, averaged over all field sizes, was 1.78% (±0.25%) and 0.94% (±0.10%) respectively. The percentage difference between the experimental and Monte Carlo calculated collimator factors for the SFD and PTWe detectors, averaged over all field sizes, was 1.29% (±0.74%) and 0.522% (±0.38%) respectively.

TABLE 2

Measured and MC simulated mini-beam collimator factor data.

| Field | Monte Carlo: $CF_{fmini}^{w}$ and $CF_{fmini}^{det}$ | | | Measured: $CF_{fmini}^{det}$ | |
|---|---|---|---|---|---|
| Size | Water | SFD | PTW$_e$ | SFD | PTW$_e$ |
| 5 × 5 | 0.429 | 0.444 | 0.422 | 0.446 | 0.422 |
| 4 × 4 | 0.436 | 0.454 | 0.429 | 0.452 | 0.427 |
| 3 × 3 | 0.441 | 0.460 | 0.435 | 0.459 | 0.432 |
| 2 × 2 | 0.451 | 0.471 | 0.442 | 0.467 | 0.438 |

Shown in Table 3 is the detector specific collimator factor corrections as detailed in Eq. [9], along with the experimental collimator factors of Table 2 corrected as detailed in Eq. [8]. The corrected collimator factors for each detector are naturally in good agreement. The more interesting detail is that the correction factors for each the two different unshielded diode detectors are disparate and suggest a respective over-response and under-response of the SFD and PTW$_e$ relative to the point dose ratio in water.

TABLE 3

Collimator factor corrections (k) and corrected experimental collimator factor data.

| Field | Monte Carlo: $k_{fmini}^{det}$ | | Corrected: $CF_{fmini}^{w} = CF_{fmini}^{det} \times k_{fmini}^{det}$ | |
|---|---|---|---|---|
| Size | SFD | PTW$_e$ | SFD | PTW$_e$ |
| 5 × 5 | 0.966 | 1.017 | 0.431 | 0.429 |
| 4 × 4 | 0.960 | 1.016 | 0.434 | 0.434 |
| 3 × 3 | 0.958 | 1.014 | 0.440 | 0.438 |
| 2 × 2 | 0.957 | 1.020 | 0.447 | 0.446 |

Example 3.0—Analysis of Experimental Results

The exemplary mini-beam collimator as designed and characterized in Examples 1.0 and 2.0 can be mounted on a commercial medical linear accelerator using the manufacturer supplied accessory tray.

In general, the agreement between simulation and measurement was good. The greatest difference between the two data sets would be certain points along the mini-beam profile (see FIGS. 14A, 14B, 14C). One can see there are clear differences in certain peak and/or valley doses, the most notable being the two valley doses on either side of the central peak and the third dose peak in from the field edge. Upon inspection it was determined that not all the grooves that the collimator blades slide into were machined at the exact beam divergence angle in the example embodiment tested in the above examples. These grooves coincide with the greatest peak and valley dose differences when compared to simulation. Even though small deficiencies were detected in the collimator build the overall quality was good with the relative point dose and collimator factor data agreeing with simulation to within the experimental uncertainty.

The agreement between the simulated, detector specific, collimator factor data and that associated with the experimental measurement were within ±2.0% and therefore are consistent with the level of agreement expected when following a dosimetric code of practice. Without being bound by theory, the slightly higher combined percentage uncertainty and percentage difference associated with the SFD detector is believed to result from an interplay effect between the small active chip area and the positional uncertainty associated with experiment. The SFD has a smaller active chip area than that of the PTW$_e$ and therefore suffers from less volume average across the central dose peak. The result of there being less volume averaging for the SFD is a greater sensitivity in measurement signal as a function of positional error—the water tank system having a constant positional uncertainty of ±0.1 mm.

The average SFD correction factor of approximately 0.960 implies a 4% detector over-response relative to that of water. Whereas the average PTW$_e$ correction factor of approximately 1.017 implies a 1.7% detector under-response relative to that of water. Both detectors are unshielded silicon diodes and therefore should produce an over-response relative to that of water (Cranmer-Sargison et al. 2011, Francescon et al. 2011 and Scott et al. 2012). However, the characteristic diode over-response relative to water has only been established using Monte Carlo simulations for square field sizes of side down to 0.25 cm (Scott et al. 2012). What is different in this work is the geometry of the very narrow central dose peak. The SFD silicon chip diameter is narrower than the width of the mini-beam collimated central dose peak (50% dose level). In contrast, the $PTW_e$ silicon chip diameter is wider than the central peak dose peak (50% dose level), which, without being bound by theory, provides a possible explanation. It is believed that the silicon chip in each detector will likely produce an over-response relative to a point dose ratio in water. However, the wider $PTW_e$ chip is believed to result in enough volume averaging to both negate the over-response and produce nearly a 2% under-response relative to a point dose ratio in water.

The dosimetric framework and supporting data presented here demonstrates that dosimetric traceability for a medical linear accelerator mounted mini-beam collimator can be established. The potential applications for mini-beam collimated radiotherapy hinge on traceability. Research into the application of mini-beam radiotherapy can now be pursued without incurring systematic errors in reported dose.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof; elements which are integrally formed may be considered to be connected or coupled;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

While a number of exemplary aspects and embodiments are discussed herein, those of skill in the art will recognize certain modifications, permutations, additions and sub-combinations thereof.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An apparatus for delivery of spatially fractionated radiation treatment to a patient, the apparatus comprising:
   a radiation source for generating an open radiation beam oriented along a beam axis and having photon energies up to and including a maximum photon energy, the maximum photon energy greater than 0.5 MV;
   a mini-beam collimator located in a path of the open radiation beam, the mini-beam collimator comprising a plurality of generally planar blades extending between an entrance aperture onto which the open beam impinges and an exit aperture, the mini-beam collimator interacting with the open radiation beam to produce an output beam emitted from the exit aperture, oriented along the beam axis and comprising a spatially fractionated mini-beam dose profile, the spatially fractionated mini-beam dose profile comprising:
   a plurality of dose peaks at which the dose is a local maximum, the dose peaks spaced apart from one another in a transverse direction that is transverse to the beam axis; and
   a plurality of dose valleys at which the dose is a local minimum, each dose valley located between a pair of transversely adjacent dose peaks.

2. An apparatus according to claim 1 comprising a beam-movement mechanism for moving the beam axis about an isocenter so that the beam axis intersects with the isocenter during the movement, the isocenter spaced apart along the beam axis from the exit aperture of the collimator.

3. An apparatus according to claim 2 wherein the radiation source is a medical linear accelerator and the beam-movement mechanism is a moveable treatment head of the medical linear accelerator.

4. An apparatus according to claim 2 wherein the maximum photon energy of the open radiation beam is selected and the blades are shaped and located relative to the radiation source and the isocenter such that the valley-to-peak dose ratio, VPDR, of the mini-beam dose profile is less than 0.80 at a surface of the skin of the patient having a tumor located at the isocenter.

5. An apparatus according to claim 2 wherein the maximum photon energy of the open radiation beam is selected and the blades are shaped and located relative to the radiation source and the isocenter such that the valley-to-peak dose ratio, VPDR, of the mini-beam dose profile is less than 0.70 at a surface of the skin of the patient having a tumor located at the isocenter.

6. An apparatus according to claim 2 wherein the maximum photon energy of the open radiation beam is selected and the blades are shaped and located relative to the radiation source and the isocenter such that a beam width of a central peak of the mini-beam dose profile in the transverse direction is in a range of 0.5 mm-2 mm at the isocenter.

7. An apparatus according to claim 2 wherein the maximum photon energy of the open radiation beam is selected and the blades are shaped and located relative to the radiation source and the isocenter such that a width of a central peak of the mini-beam dose profile in the transverse direction is in a range of 0.7 mm-1.5 mm at the isocenter.

8. An apparatus according to claim 2 wherein the maximum photon energy of the open radiation beam is selected and the blades are shaped and located relative to the radiation source and the isocenter such that a peak-to-peak separation between a central peak of the mini-beam dose profile and a transversely adjacent peak in the transverse direction is in a range of 1.5 to 5 times a beam width of the central peak in the transverse direction at the isocenter.

9. An apparatus according to claim 2 wherein the maximum photon energy of the open radiation beam is selected and the blades are shaped and located relative to the radiation source and the isocenter such that a peak-to-peak separation between a central peak of the mini-beam dose profile and a transversely adjacent peak in the transverse direction is in a range of 2 to 4 times a beam width of the central peak in the transverse direction at the isocenter.

10. An apparatus according to claim 2 wherein the entrance aperture of the collimator is located at a distance, along the beam axis, in a range of 40 cm-80 cm from the radiation source.

11. An apparatus according to claim 1 wherein the maximum photon energy is in a range of 4 MV-25 MV.

12. An apparatus according to claim 1 wherein the radiation source is a Cobalt-60 radiation source.

13. An apparatus according to claim 12 wherein the maximum photon energy is in a range of 4 MV-10 MV.

14. An apparatus according to claim 1 wherein the collimator comprises a central collimator axis about which the blades are symmetrically located and wherein the collimator is located so that the central collimator axis is aligned with the beam axis.

15. An apparatus according to claim 14 wherein the blades are spaced apart from one another in the transverse direction by air gaps.

16. An apparatus according to claim 14 wherein the blades are oriented such that widths of the air gaps in the transverse direction at the exit aperture are greater than widths of the air gaps in the transverse direction at the entrance aperture.

17. An apparatus according to claim 14 wherein the blades are oriented at a variety of angles relative to the collimator axis.

18. An apparatus according to claim 14 wherein a transversely outermost pair of blades are respectively oriented at angles +/−θ relative to the collimator axis, where θ corresponds to the divergence angle of the open beam.

19. An apparatus according to claim 14 comprising one or more adjustment mechanisms for locating the collimator relative to the radiation source.

20. An apparatus according to claim 1 wherein the blades comprise lengths in directions of extension of the blades between the entrance aperture and the exit aperture in a range of 1 cm-25 cm.

21. An apparatus according to claim 1 wherein the blades comprise lengths in directions of extension of the blades between the entrance aperture and the exit aperture in a range of 2 cm-10 cm.

22. An apparatus according to claim 1 wherein the blades comprise widths in directions transverse to their extension between the entrance aperture and the exit aperture in a range of 0.4 mm-6.0 mm.

23. An apparatus according to claim 1 wherein the blades comprise widths in directions transverse to their extension between the entrance aperture and the exit aperture in a range of 0.6 mm-1.0 mm.

24. An apparatus according to claim 1 wherein the maximum photon energy of the open radiation beam is selected and the blades are shaped and located relative to the radiation source and the isocenter such that the valley-to-peak dose ratio, VPDR, of the mini-beam dose profile is less than 0.85 at a depth into the patient that is equivalent to a depth of 10 cm into water.

25. An apparatus according to claim 1 wherein the maximum photon energy of the open radiation beam is selected and the blades are shaped and located relative to the radiation source and the isocenter such that the valley-to-peak dose ratio, VPDR, of the mini-beam dose profile is less than 0.80 at a depth into the patient that is equivalent to a depth of 10 cm into water.

26. A method for generating spatially fractionated radiation, the method comprising:
  generating an open radiation beam oriented along a beam axis and having photon energies up to and including a maximum photon energy, the maximum photon energy greater than 0.5 MV;
  positioning a mini-beam collimator in a path of the open radiation beam, the mini-beam collimator comprising a plurality of generally planar blades extending between an entrance aperture onto which the open beam impinges and an exit aperture,
  producing, by interaction of the mini-beam collimator with the open radiation beam, an output beam emitted from the exit aperture, oriented along the beam axis and comprising a spatially fractionated mini-beam dose profile, the spatially fractionated mini-beam dose profile comprising:
  a plurality of dose peaks at which the dose is a local maximum, the dose peaks spaced apart from one another in a transverse direction that is transverse to the beam axis; and
  a plurality of dose valleys at which the dose is a local minimum, each dose valley located between a pair of transversely adjacent dose peaks.

27. A method for treating a tumor in a patient using spatially fractionated radiation, the method comprising:
  generating an open radiation beam oriented along a beam axis and having photon energies up to and including a maximum photon energy, the maximum photon energy greater than 0.5 MV;
  positioning a mini-beam collimator in a path of the open radiation beam, the mini-beam collimator comprising a plurality of generally planar blades extending between an entrance aperture onto which the open beam impinges and an exit aperture,
  producing, by interaction of the mini-beam collimator with the open radiation beam, an output beam emitted from the exit aperture, oriented along the beam axis and comprising a spatially fractionated mini-beam dose profile, the spatially fractionated mini-beam dose profile comprising:

a plurality of dose peaks at which the dose is a local maximum, the dose peaks spaced apart from one another in a transverse direction that is transverse to the beam axis; and a plurality of dose valleys at which the dose is a local minimum, each dose valley located between a pair of transversely adjacent dose peaks; and.

locating the patient along the beam axis, so that the output beam impinges on the patient, thereby delivering the spatially fractionated mini-beam dose profile to the patient.

* * * * *